(12) United States Patent
Bae et al.

(10) Patent No.: US 8,187,727 B2
(45) Date of Patent: May 29, 2012

(54) IMIDAZOLE DERIVATIVES, PREPARATION METHOD THEREOF AND ORGANIC ELECTRONIC DEVICE USING THE SAME

(75) Inventors: Jae Soon Bae, Daejeon (KR); Dong Hoon Lee, Seoul (KR); Dae Woong Lee, Daejeon (KR); Jun Gi Jang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 854 days.

(21) Appl. No.: 11/488,089

(22) Filed: Jul. 18, 2006

(65) Prior Publication Data

US 2007/0018155 A1    Jan. 25, 2007

(30) Foreign Application Priority Data

Jul. 22, 2005   (KR) .................. 10-2005-0066730

(51) Int. Cl.
*H01L 51/54* (2006.01)
*C07D 235/02* (2006.01)
*C07D 401/00* (2006.01)
*C07D 403/00* (2006.01)
*C07D 409/00* (2006.01)
*C09K 11/06* (2006.01)

(52) U.S. Cl. ..... 428/690; 428/917; 313/502; 548/302.1; 548/311.1; 548/311.4

(58) Field of Classification Search .................. 428/690
See application file for complete search history.

(56) References Cited

U.S. PATENT DOCUMENTS

| 3,050,389 | A | | 8/1962 | Süs et al. | |
|---|---|---|---|---|---|
| 2004/0023060 | A1 | * | 2/2004 | Kim et al. | 428/690 |
| 2005/0064240 | A1 | * | 3/2005 | Mishima et al. | 428/690 |

FOREIGN PATENT DOCUMENTS

| CN | 1775779 | A | * | 5/2006 |
|---|---|---|---|---|
| EP | 0276942 | A1 | | 8/1988 |
| EP | 0426021 | A1 | | 10/1990 |
| JP | 2001097949 | A | * | 4/2001 |
| JP | 2001247858 | A | * | 9/2001 |
| WO | WO 90/09997 | A1 | | 9/1990 |
| WO | WO 03/012890 | | | 2/2003 |
| WO | WO 03/072099 | A1 | | 9/2003 |
| WO | WO 03072099 | A1 | * | 9/2003 |

OTHER PUBLICATIONS

Machine translation of JP2001-097949. Apr. 2001.*
Machine translation of JP2001-247858. Sep. 2001.*
Machine translation of CN 1775779. May 2006.*
Prasanna A. et al., "A 3D-QSAR of Angiotensin II(ATI) Receptor Antagonists Based on Receptor Surface Analysis", J. Chem. Inf. Comput. Sci., 2004, 44(1), pp. 210-220.
Lawrence et al., "Synthesis and Substance P Antagonist Activity of Naphthimidazolium Derivatives", J. Med. Chem. 1992, 35, pp. 1273-1279.
G.E. Grella, et al., "Synthesis and cytotoxicity of substituted 2-benzylnaphth[2,3-d]imidazoles", European Journal of Pharmaceutical Sciences, 2003, vol. 20, p. 267-272.
Lev M. Yagupolskii, et al., "2-Alkyl-1-(2-aryl-1,1-difluoro-2-hydroxyethyl)benzimidazoles: potential angiotensin II receptor antagonists", Tetrahedron Letters, 2000, vol. 41, p. 2265-2267.
Abdullah Hijazi, "Nucleosides, III[1] Synthesis and Properties of 2-Trifluoromethyl-Naphthimidazole-Ribonucleoside", Nucleosides & Nucleotides, 1986, vol. 5, No. 5, p. 529-537.

* cited by examiner

*Primary Examiner* — Lynda M Salvatore
*Assistant Examiner* — Andrew K Bohaty
(74) *Attorney, Agent, or Firm* — McKenna Long & Aldridge LLP

(57) ABSTRACT

The present invention relates to a new imidazole derivative, a method for preparing the derivative, and an organic electronic device using the derivative. The imidazole derivative according to the invention can perform functions of hole injection, hole transportation, electron injection, electron transportation, and/or light emission in an organic electronic device including an organic light-emitting device. The organic electronic device according to the invention exhibits excellent characteristics in terms of efficiency, drive voltage and stability.

12 Claims, 1 Drawing Sheet

UV spectrum of formula(1-10)

IMIDAZOLE DERIVATIVES, PREPARATION METHOD THEREOF AND ORGANIC ELECTRONIC DEVICE USING THE SAME

TECHNICAL FIELD

The present invention relates to a new imidazole derivative, a method for preparing the same and an organic electronic device using the same.

This application claims the benefit of the filing date of Korean Patent Application Nos. 10-2005-0066730, filed on Jul. 22, 2005, in the Korean Intellectual Property Office, the disclosure of which is incorporated herein in its entirety by reference.

BACKGROUND ART

The term "organic electronic device" as used in the present specification refers to a device requiring charge exchange between an electrode and an organic material, using holes and/or electrons. The organic electronic device can be largely classified into two types according to its operational principle as follows: One type is an electronic device having a configuration in which an exciton is formed in an organic material layer by photons flown from an external light source into the device and the exciton is separated into an electron and a hole, the electron and the hole are transported to a different electrode, respectively and used as a current source (voltage source), and the other type is an electronic device having a configuration in which a hole and/or electron are/is injected into an organic material semiconductor forming an interface with an electrode by applying a voltage or current to two or more electrodes to allow the device to operate by means of the injected electron and hole.

Examples of the organic electronic device include an organic light-emitting device, an organic solar cell, an organic photoconductor (OPC) drum and an organic transistor, which all require a hole-injecting or hole-transporting material, an electron-injecting or electron-transporting material, or a light-emitting material for driving the device. Hereinafter, the organic light-emitting device will be mainly and specifically described, but in the above-mentioned organic electronic devices, the hole-injecting or hole-transporting material, the electron-injecting or electron-transporting material, or the light-emitting material injection functions according to a similar principle.

In general, the term "organic light-emitting phenomenon" refers to a phenomenon in which electric energy is converted to light energy by means of an organic material. The organic light-emitting device using the organic light-emitting phenomenon has a structure usually comprising an anode, a cathode and an organic material layer interposed there between. Herein, the organic material layer may be mostly formed in a multilayer structure comprising layers of different materials, for example, the hole-injecting layer, the hole-transporting layer, the light-emitting layer, the electron-transporting layer, the electron-injecting layer and the like, in order to improve efficiency and stability of the organic light-emitting device. In the organic light-emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such an organic light-emitting device is known to have characteristics such as self-luminescence, high brightness, high efficiency, low drive voltage, wide viewing angle, high contrast and high-speed response.

The materials used for the organic material layer of the organic light-emitting device can be classified into a light-emitting material and a charge-transporting material, for example, a hole-injecting material, a hole-transporting material, an electron-transporting material and an electron-injecting material, according to their functions. Further, the light-emitting material can be divided into a blue, green or red light-emitting material and a yellow or orange light-emitting material required for giving more natural color, according to a light-emitting color. On the other hand, when only one material is used for the light-emitting material, an efficiency of a device is lowered owing to maximum luminescence wavelength moved to a longer wavelength, deterioration of color purity, or reduction in light emitting efficiency, due to the interaction between molecules, and therefore a host/dopant system can be used as the light-emitting material for the purpose of enhancing color purity and light emitting efficiency through energy transfer.

In order to allow the organic light-emitting device to fully exhibit the above-mentioned excellent characteristics, a material constituting the organic material layer in the device, for example, a hole-injecting material, a hole-transporting material, a light-emitting material, an electron-transporting material and an electron-injecting material should be essentially composed of a stable and efficient material. However, the development of a stable and efficient organic material layer material for the organic light-emitting device has not yet been fully realized. Accordingly, the development of new materials is continuously desired. The development of such a material is equally required to the above-mentioned other organic electronic devices.

DISCLOSURE

Technical Problem

The present inventors have found an imidazole derivative having a new structure and found that the derivative can perform functions of hole injection, hole transportation, electron injection, electron transportation, and/or light emission in an organic electronic device including an organic light-emitting device.

Accordingly, it is an object of the present invention to provide an imidazole derivative having a new structure, a method for preparing the derivative, and an organic electronic device using the derivative.

Technical Solution

The present invention provides an imidazole derivative represented by the following formula (1):

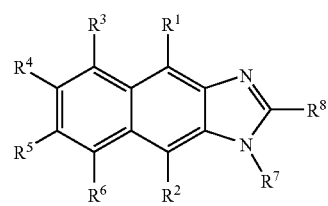

(1)

wherein $R^1$ to $R^6$ are each independently or simultaneously selected from the group consisting of a hydrogen atom, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a substituted or unsubstituted aliphatic cyclic group, a substituted or unsubstituted silicon group, a substituted or unsubstituted boron group, an amino group, a nitrile group, a nitro group, a halogen group, an amide group and an ester group;

$R^7$ is selected from the group consisting of a substituted or unsubstituted alkyl group, a substituted or unsubstituted aryl group, a substituted or unsubstituted heterocyclic group, a substituted or unsubstituted aliphatic cyclic group, and a substituted or unsubstituted silicon group; and $R^8$ is selected from the group consisting of a substituted or unsubstituted alkyl group, a substituted or unsubstituted aryl group, and a substituted or unsubstituted heterocyclic group.

Further, the invention provides an organic electronic device comprising a first electrode, a second electrode and at least one organic material layer arranged between the first electrode and the second electrode, in which the at least one layer of the organic material layer comprises the compound represented by the above formula (1).

Hereinafter, the compound of the invention will be explained in detail.

The compound of the above formula (1) is a new compound and substituents thereof are explained in detail in the following.

The alkyl group of $R^1$ to $R^8$ in the above formula (1) preferably have 1 to 30 carbon atoms.

The alkoxy group and alkenyl group of $R^1$ to $R^6$ in the above formula (1) preferably have 1 to 30 carbon atoms.

Examples of the aryl group of $R^1$ to $R^8$ in the above formula (1) include, but are not limited to, a phenyl group, a naphthyl group, an anthracenyl group, a biphenyl group, a pyrenyl group and a perylenyl group.

Examples of the arylamine group of $R^1$ to $R^6$ in the above formula (1) include, but are not limited to, a diphenylamine group, a phenylnaphtylamine group, a ditolylamine group, a phenyltolylamine group, a carbazolyl group and a triophenylamine group.

Examples of the heterocyclic group of $R^1$ to $R^8$ in the above formula (1) include, but are not limited to, a pyridyl group, a bipyridyl group, an acridinyl group, a thienyl group, an imidazolyl group, an oxazolyl group, a thiazolyl group and a quinolyl group.

Examples of the halogen group of $R^1$ to $R^6$ in the above formula (1) include fluorine, chlorine, bromine and iodine.

In the invention, $R^7$ is preferably selected from the group consisting of a substituted or unsubstituted alkyl group, a substituted or unsubstituted cycloalkyl group, a substituted or unsubstituted aryl group, and a substituted or unsubstituted heteroaryl group. Examples of the alkyl group include a methyl group, an ethyl group, a propyl group, an isopropyl group, a butyl group, a tert-butyl group, a pentyl group, a hexyl group and a heptyl group. Examples of the cycloalkyl group include a cyclopentyl group, a cyclohexyl group and the like. Examples of the alkyl group or cycloalkyl group include, but are not limited to, those having 1 to 30 carbon atoms which provide no steric hindrance. Examples of the aryl group preferably include a phenyl group, a biphenyl group and a naphthyl group, and a heteroaryl group such as a pyridyl group, a bipyridyl group, a quinolyl group and an isoquinolyl group is also preferred.

In the invention, when $R^1$ to $R^8$ in the formula (1) are substituted with other substituents, these substituents are preferably at least one selected from —CN, a nitro group, a carbonyl group, an amide group, an alkyl group, an alkenyl group, an aryl group, an arylamine group, a heterocyclic group, an aliphatic cyclic group, —BRR' and —SiRR'R" (wherein R, R' and R" are the same or different from each other and are independently selected from a $C_1$ to $C_{20}$ alkyl group, a $C_6$ to $C_{20}$ aryl group, or a $C_6$ to $C_{20}$ aryl group substituted with a $C_1$ to $C_{20}$ alkyl group). The alkyl group is preferably $C_1$ to $C_{20}$, the alkenyl group is preferably $C_2$ to $C_{20}$. The aryl group is preferably $C_6$ to $C_{20}$ and the arylamine group is preferably an amine group substituted with a $C_6$ to $C_{20}$ aryl group. The compound of the above formula (1) does not vary in its properties depending on the above-mentioned core structures according to the kinds of the substituents when the compound has the above-mentioned substituents. In the invention, when $R^1$ to $R^8$ in the formula (1) are substituted with other substituents, OH is excluded from the substituents.

In the above formula (1), preferably, $R^1$ and $R^2$ are each selected from the group consisting of a hydrogen atom, a substituted or unsubstituted aryl group, a substituted or unsubstituted alkenyl group, a substituted or unsubstituted arylamine group, and a substituted or unsubstituted heterocyclic group, provided that $R^1$ and $R^2$ are not simultaneously a hydrogen atom;

$R^3$ to $R^6$ are each selected from the group consisting of a hydrogen atom, a nitrile group, a substituted or unsubstituted aryl group, a substituted or unsubstituted arylamine group, and a substituted or unsubstituted heterocyclic group;

$R^7$ is selected from the group consisting of an alkyl group and an aryl group such as a phenyl group, a biphenyl group and a naphthyl group; and $R^8$ is selected from the group consisting of a substituted or unsubstituted alkyl group, a substituted or unsubstituted aryl group, and a substituted or unsubstituted heterocyclic group.

In the above formula (1), more preferably, $R^1$, $R^2$ and $R^8$ are each selected from the group consisting of an aryl group and a heterocyclic group;

$R^3$ to $R^6$ are a hydrogen atom; and $R^7$ is selected from the group consisting of an alkyl group and an aryl group.

The following illustrates specific examples of the compound of the formula (1), but the scope of the invention is not limited only thereto.

(1-1)

-continued
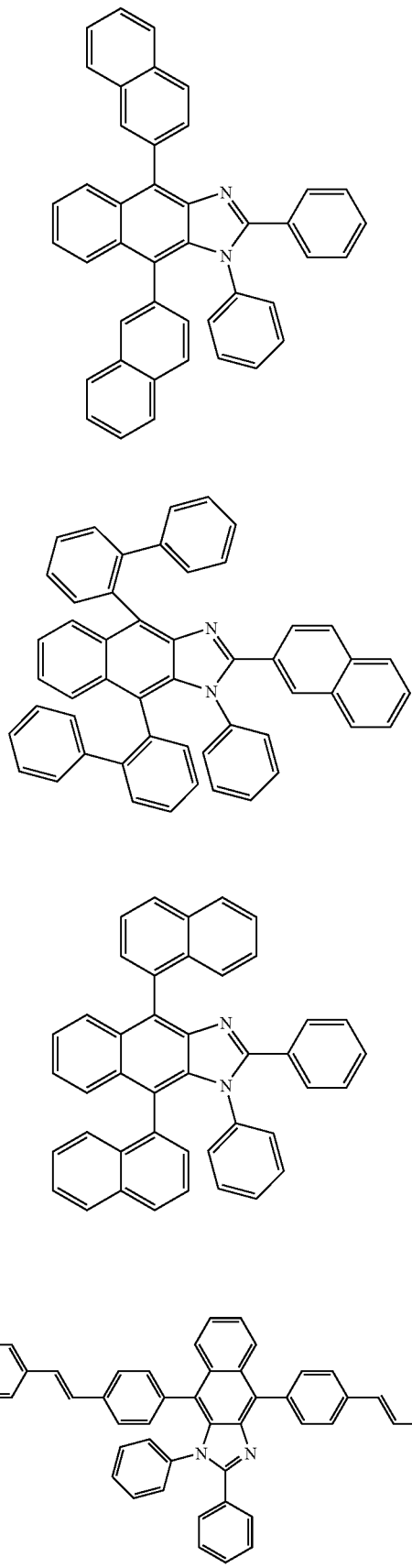
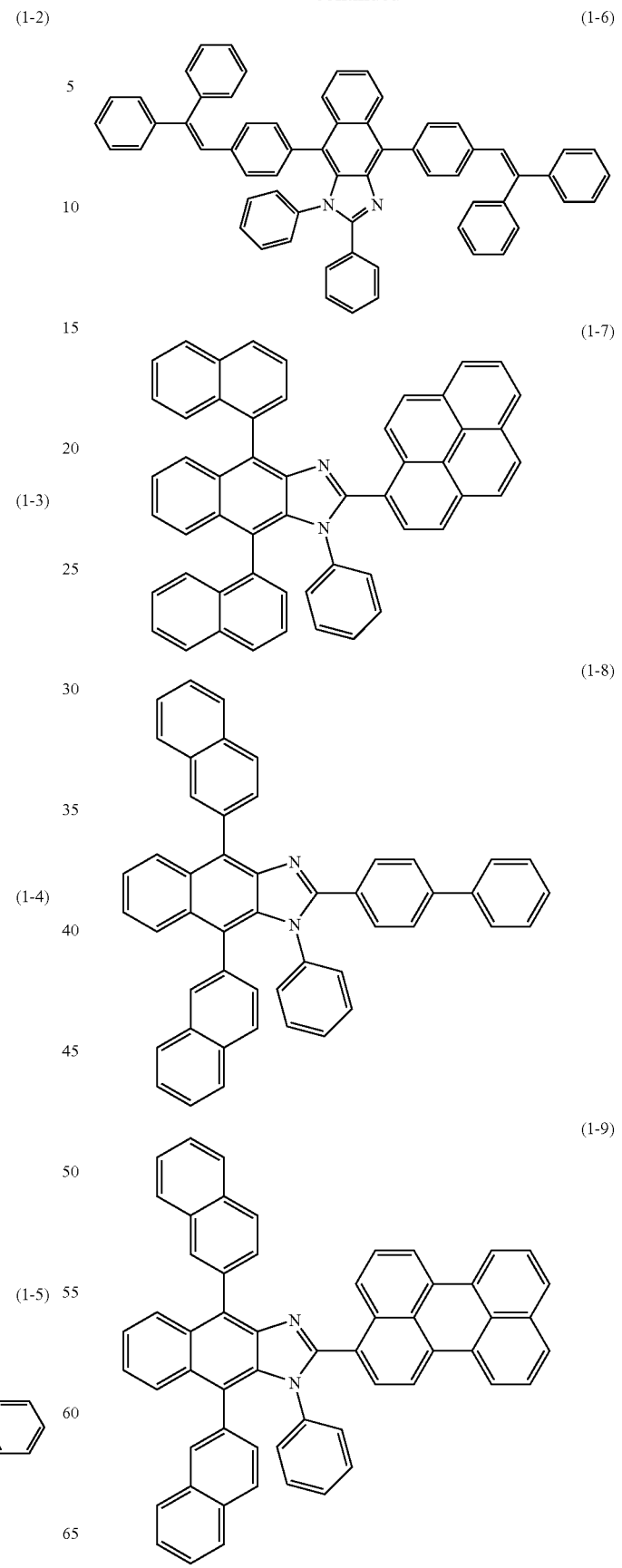

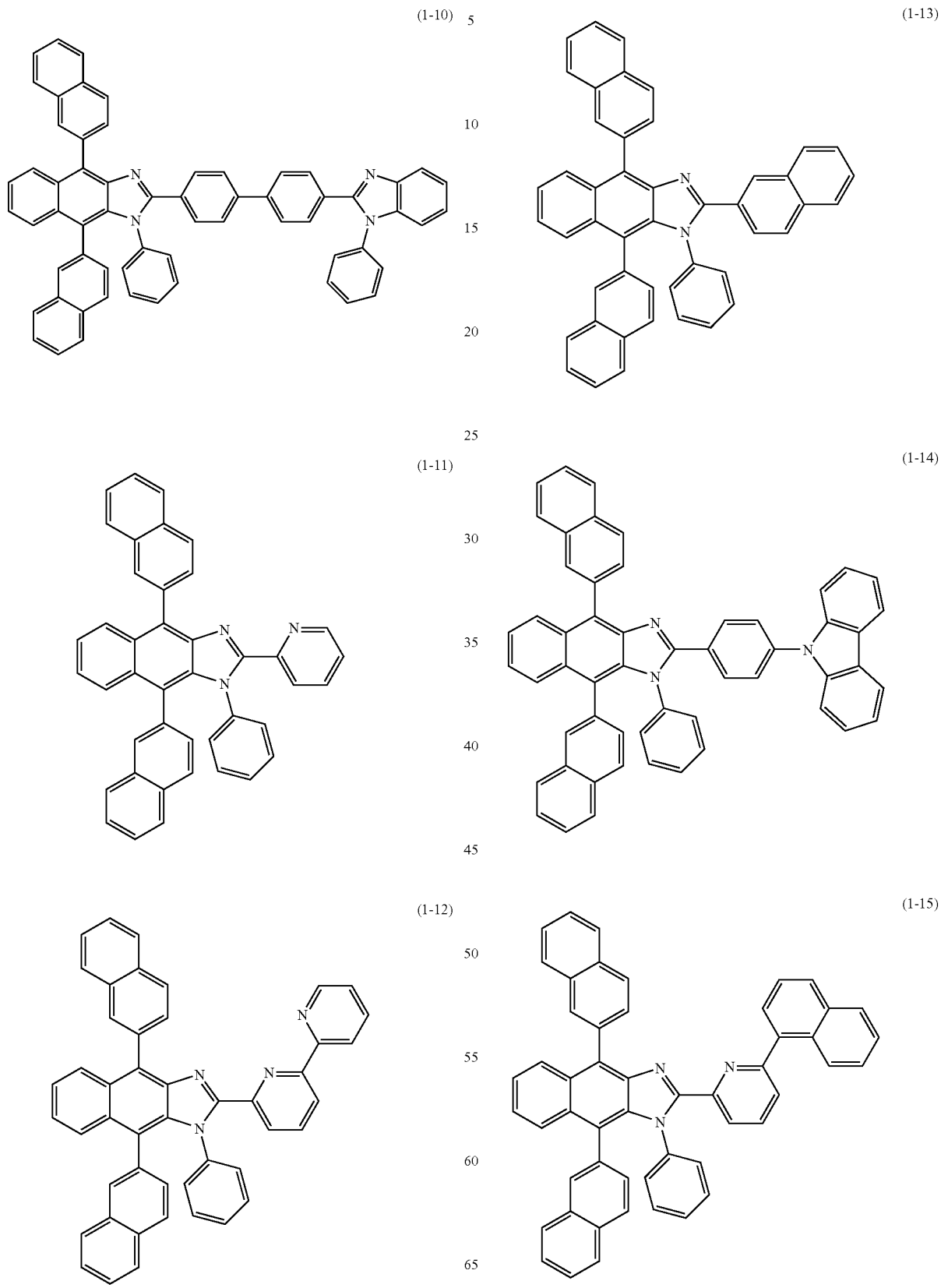

(1-16)
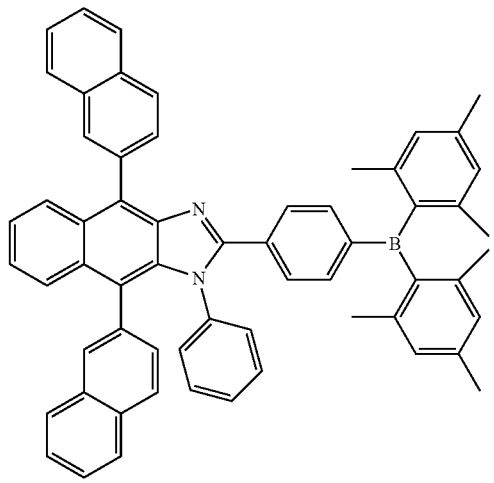
(1-17)
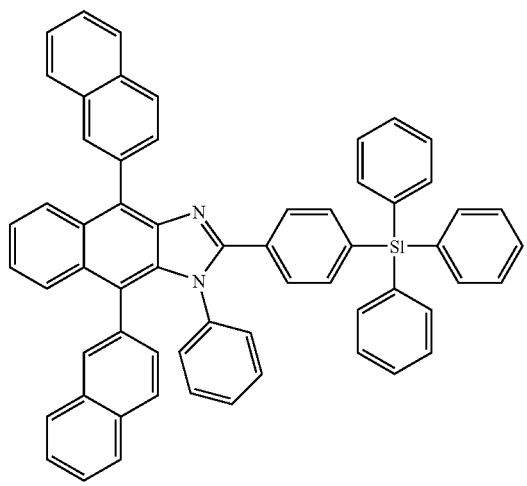
(1-18)
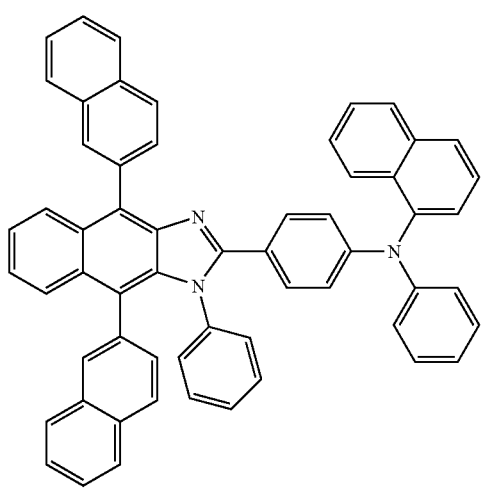
(1-19)
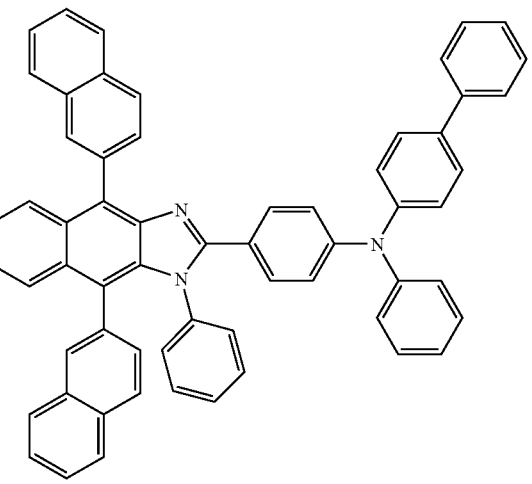
(1-20)
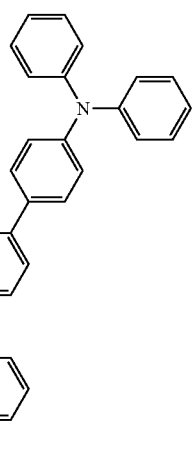
(1-21)
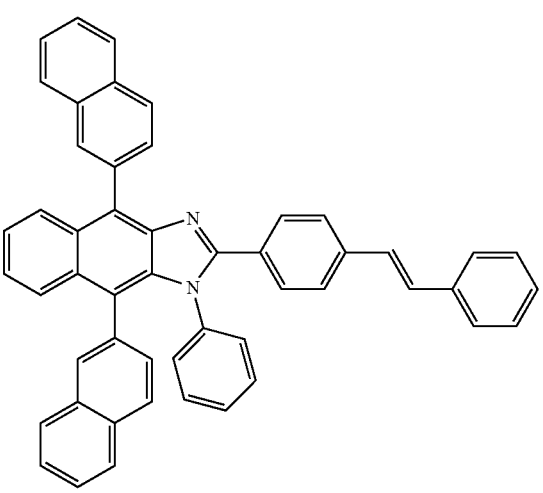

(1-22)
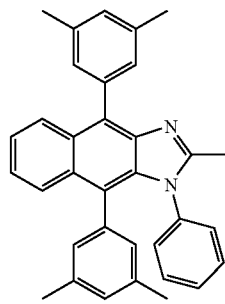
(1-25)
(1-26)
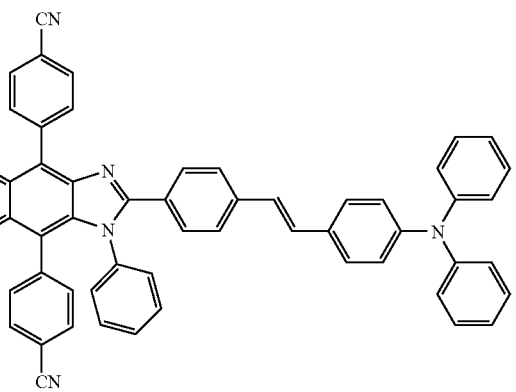
(1-23)
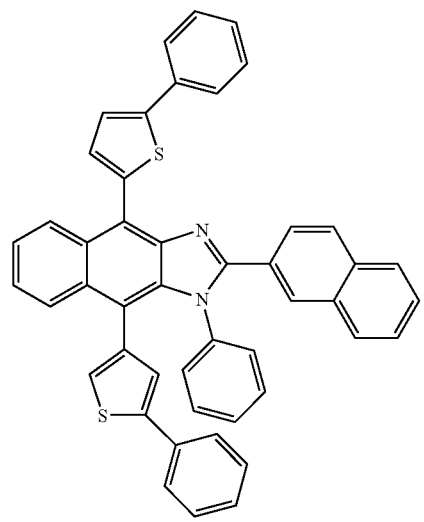
(1-27)
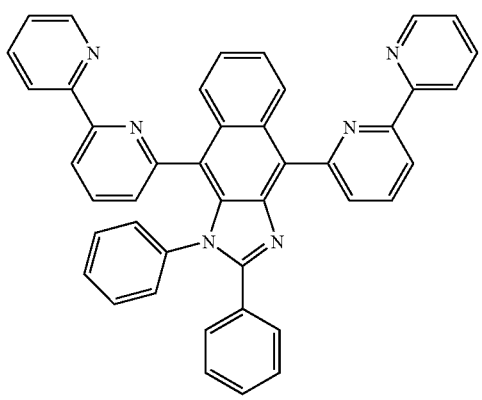
(1-24)
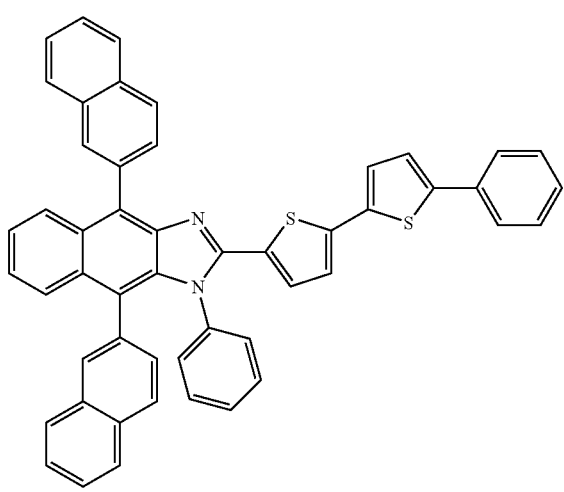
(1-28)
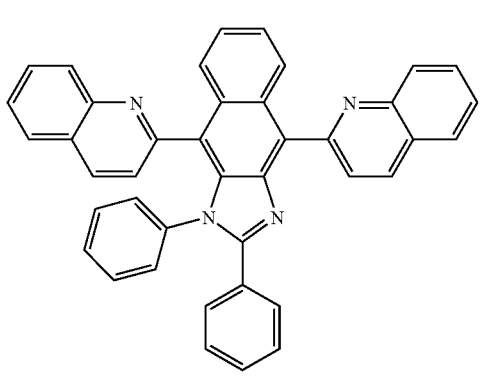

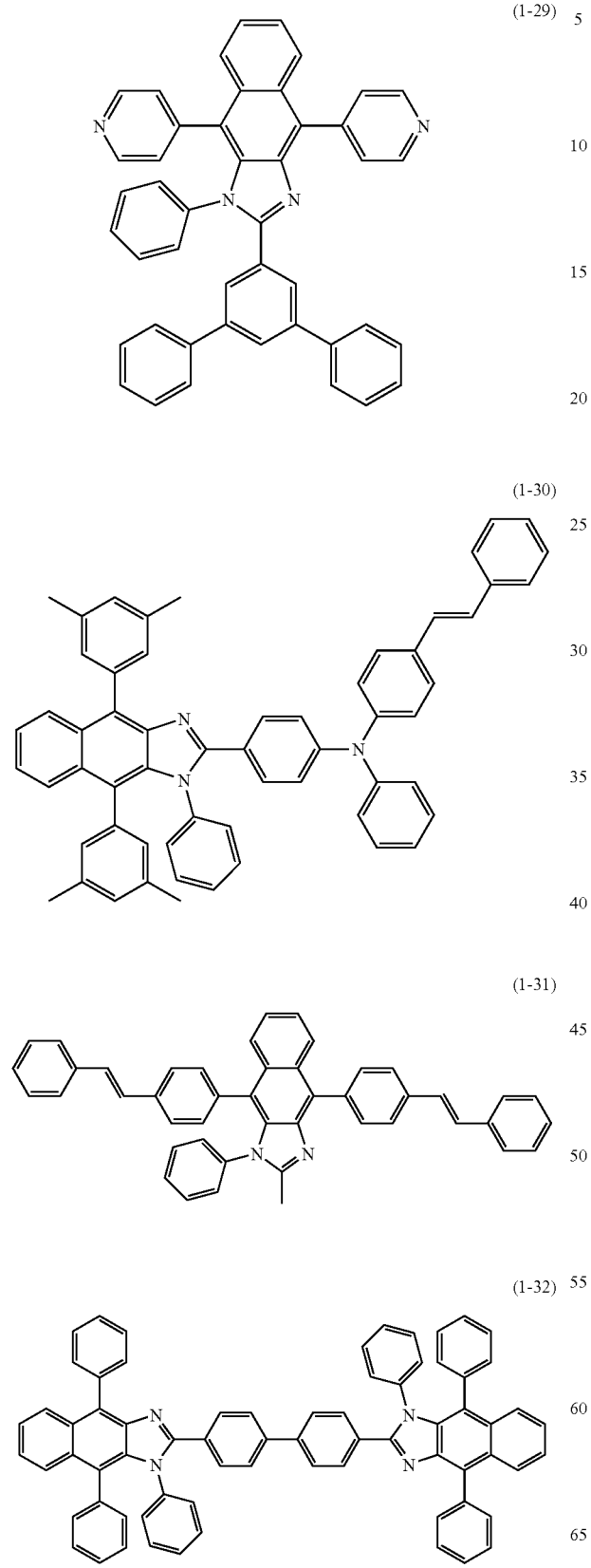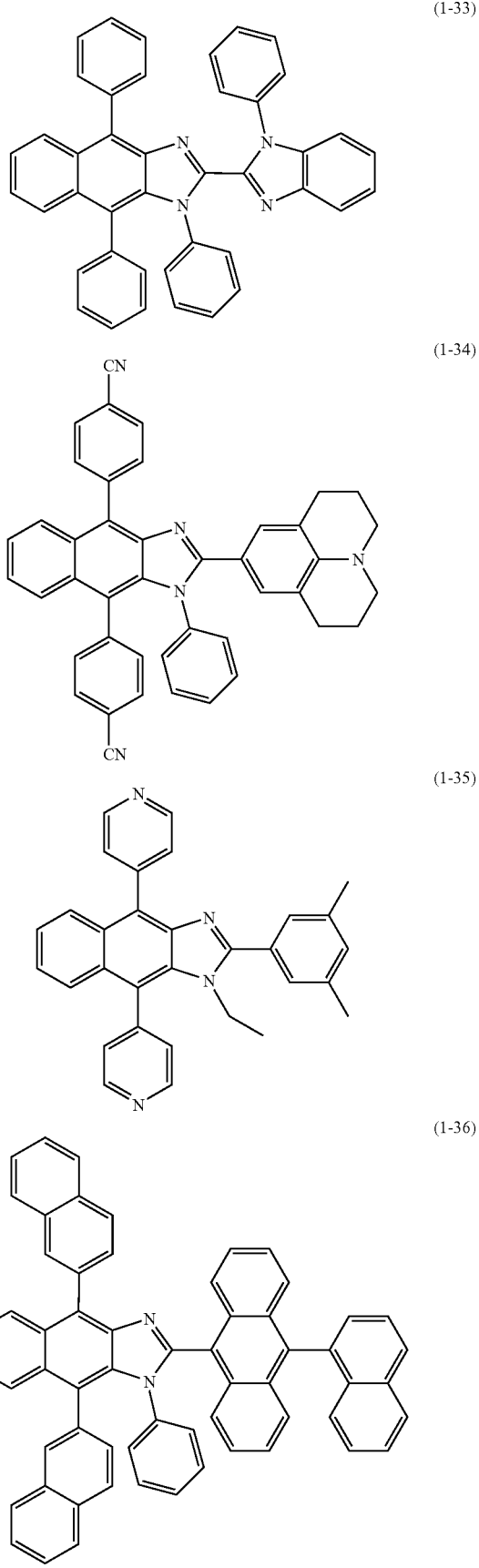

(1-37)
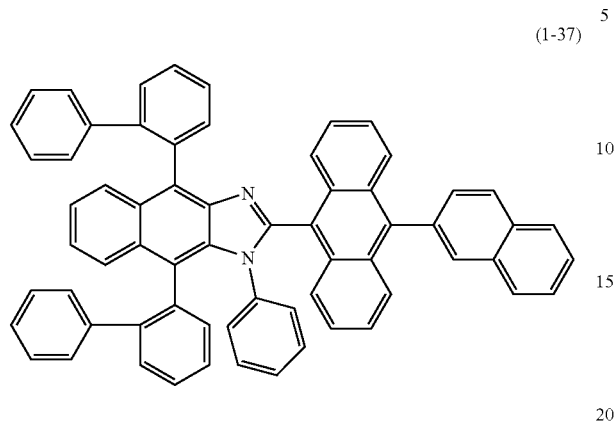
(1-40)
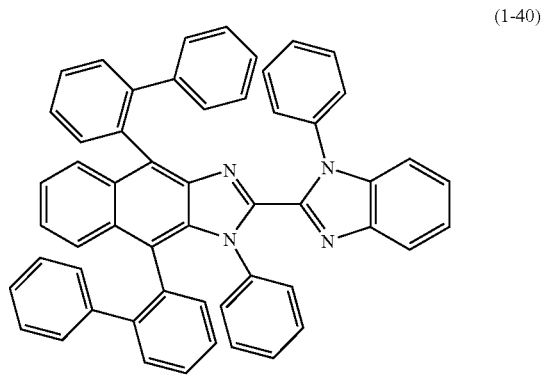
(1-38)
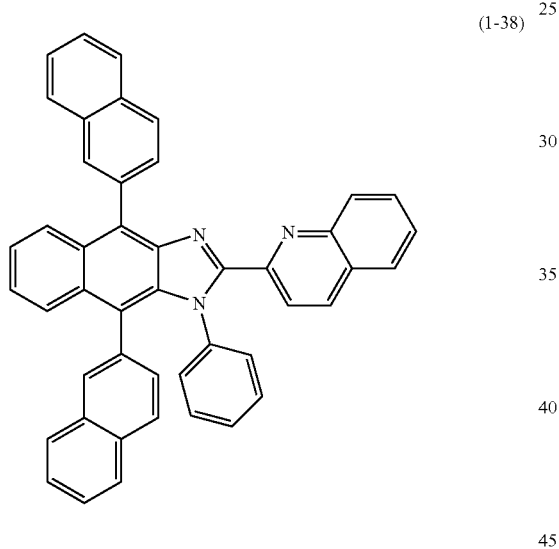
(1-41)
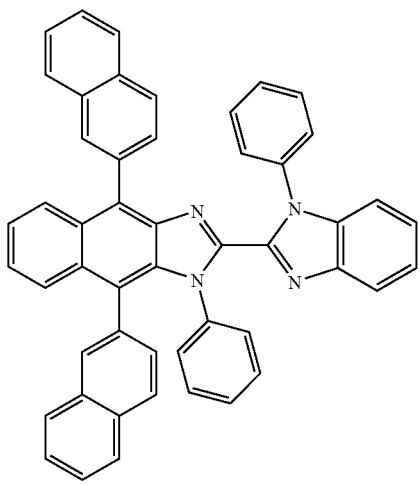
(1-39)
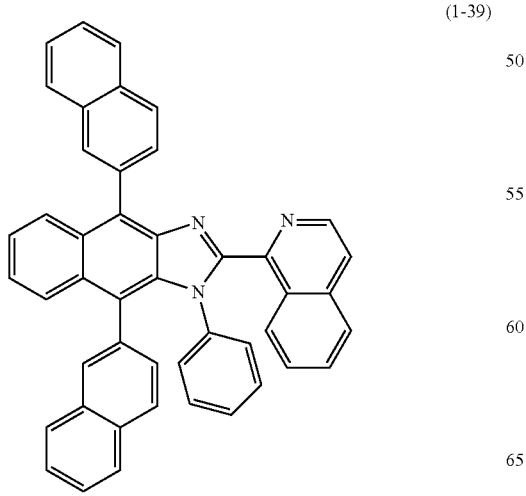
(1-42)
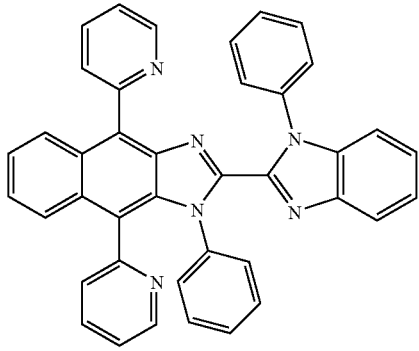

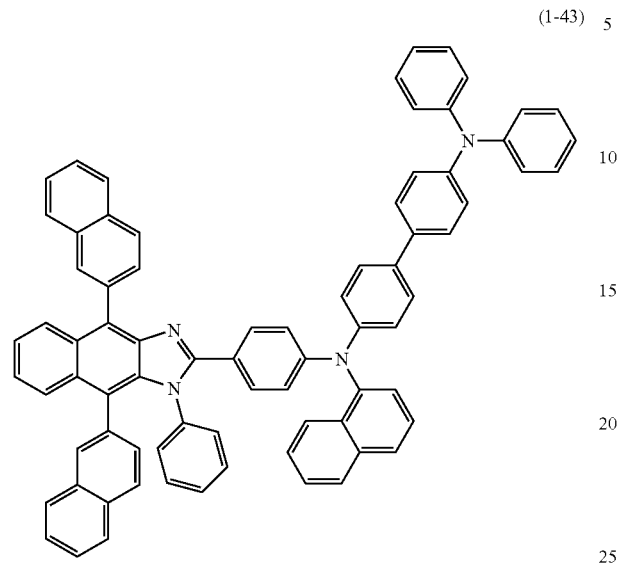
(1-43)
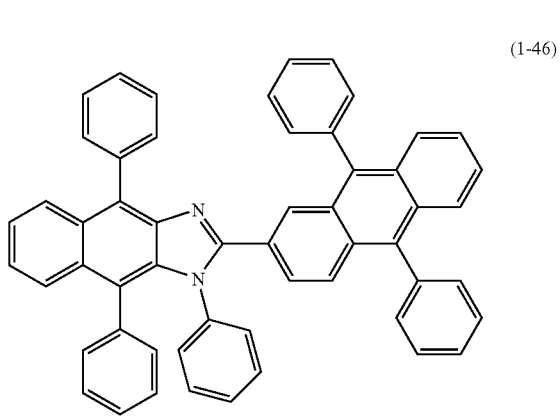
(1-46)
(1-44)
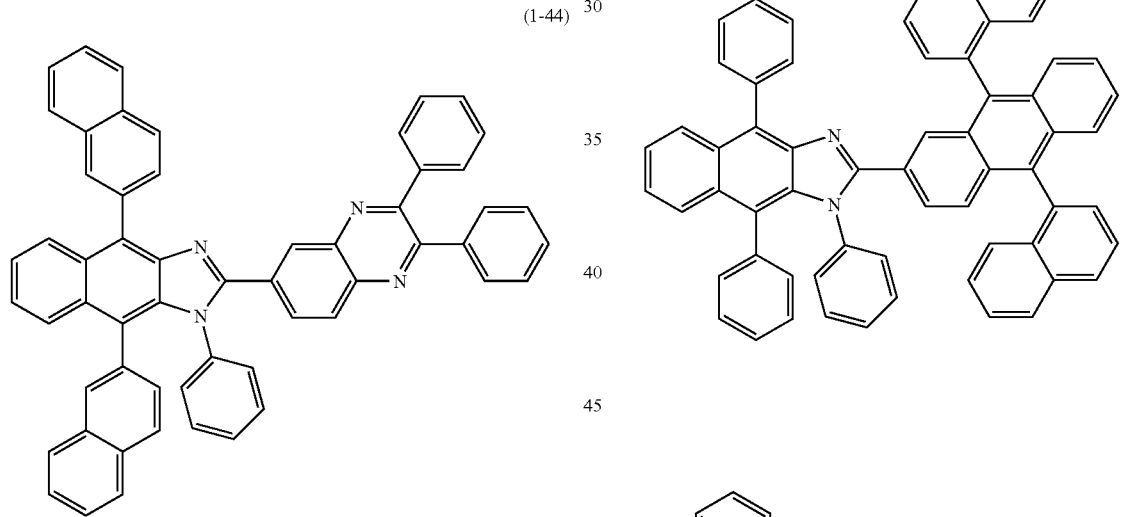
(1-47)
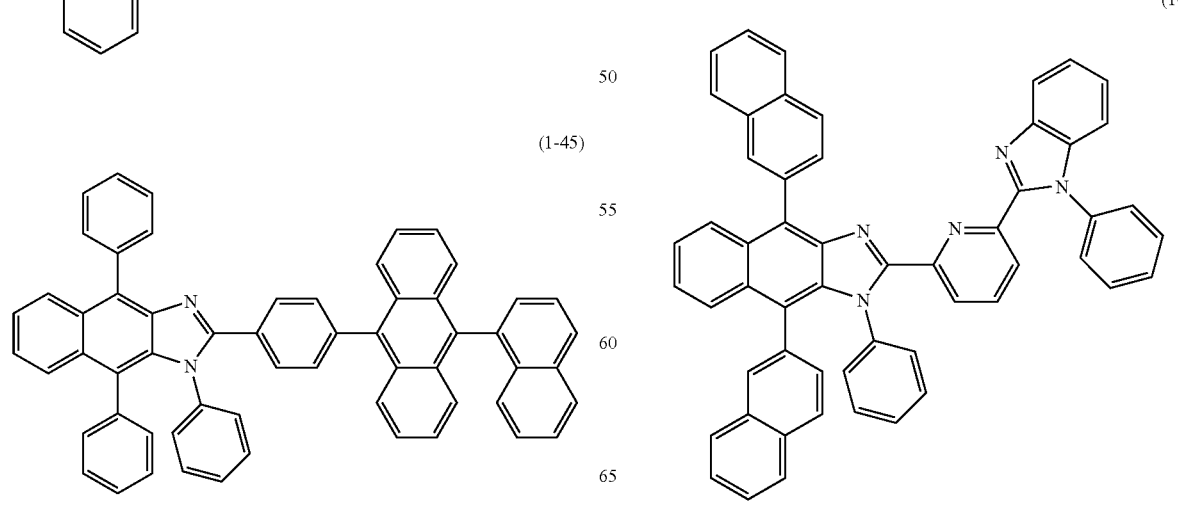
(1-45)
(1-48)

(1-49)

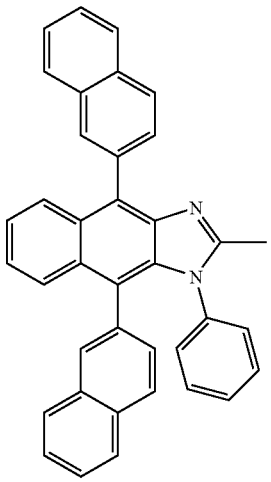

(1-50)

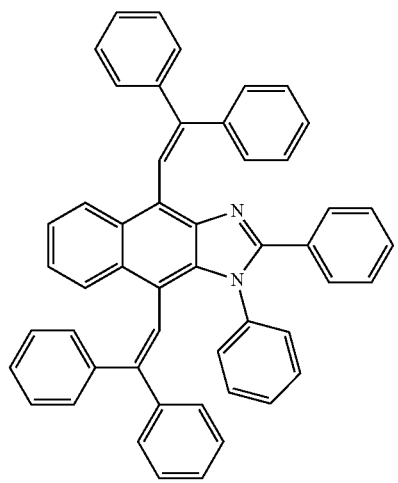

(1-51)

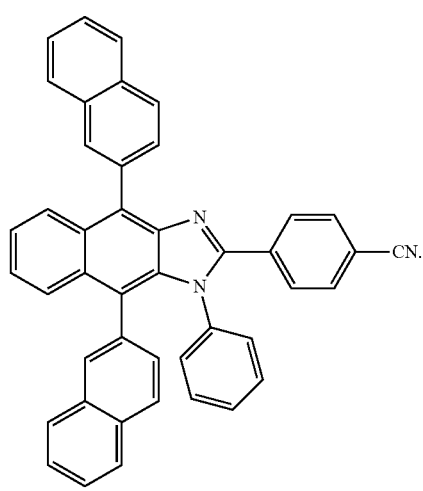

Further, the invention provides a method for preparing an imidazole derivative represented by the above formula (1).

The above-mentioned compounds according to the invention can be prepared as follows.

For example, the compound of the above formula (1) can be prepared by a method comprising the steps of:

a) introducing each of an amino group having $R^7$ and an amino group ($NH_2$), respectively, at the 2- and the 3-carbon position of a substituted or unsubstituted naphthoquinone and introducing $R^8$ at the amino group ($NH_2$);

b) forming an imidazole group by linking chains of the portions at which $R^7$ and $R^8$ are introduced, of the compound obtained in the above a);

c) converting the compound obtained in the above b) to a dialcohol derivative; and d) reducing the compound obtained in the above c) to form a naphthalene group.

In addition, the compound of the above formula (1) can be prepared by a method comprising the steps of:

a) introducing each of an amino group having $R^7$ and an amino group ($NH_2$), respectively, at the 2- and the 3-carbon position of a substituted or unsubstituted naphthoquinone and introducing $R^8$ at the amino group ($NH_2$);

b) forming an imidazole group by linking chains of the portions at which $R^7$ and $R^8$ are introduced, of the compound obtained in the above a);

c) reducing the compound obtained in the above b) to form a naphthalene group;

d) introducing a bromo group at the 8- or the 9-carbon position of the compound obtained in the above c); and e) introducing a substituent at the position of the compound obtained in the above d), in which a bromo group is introduced, with boronic acid.

In the above-mentioned method, a step of d) introducing a bromo group can be conducted by reacting the compound with N-bromosuccinimide or bromine ($Br_2$) in a solvent such as dimethylformamide (DMF), chloroform ($CHCl_3$) and acetic acid.

The above-mentioned method is different from a method for preparing a compound in which a hydrogen atom is present at the position of $R^7$ in the above formula (1). That is, the substituent of $R^7$ in the compound of the formula (1) according to the invention is derived from an amine group, and hence, the compound of the invention is different from the compound in which a hydrogen atom is present at the position of $R^7$ in the above formula (1).

Specifically, the compound of the above formula (1) can be prepared according to the following reaction scheme 1:

Reaction Scheme 1

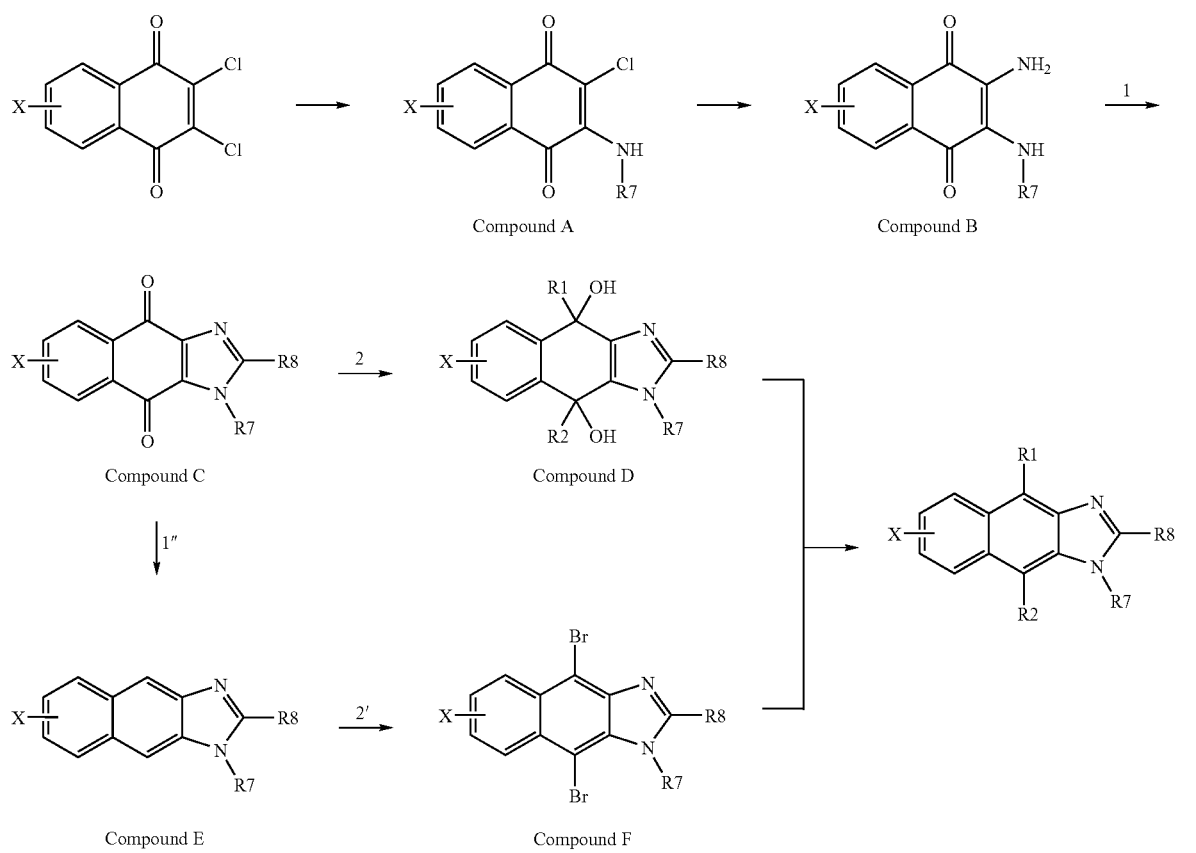

wherein X is selected from the group consisting of a hydrogen atom, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a substituted or unsubstituted aliphatic cyclic group, a substituted or unsubstituted silicon group, a substituted or unsubstituted boron group, an amino group, a nitrile group, a nitro group, a halogen group, an amide group and an ester group, and two or more X's may exist and when two or more X's exist, they may be different from one another; and $R^1$, $R^2$, $R^7$ and $R^8$ are as defined in the above formula (1).

Specifically, the compound of the invention can be prepared as follows. The compound A is prepared by reacting a substituted or unsubstituted 2,3-dichloronaphthoquinone, as the starting material, with a primary amine group having a $R^7$ substituent and acetic acid. Subsequently, the compound B is prepared by reacting the compound A with sodium azide (NaN$_3$), dimethylformamide (DMF) and water. Then, the compound C is prepared by reacting the compound B with a $R^8$ substituent having a formyl group introduced therein and dimethylacetamide (DMAC) (1). Herein, the $R^8$ substituent having the formyl group introduced therein may be the following groups, each of which has a formyl group introduced therein, and the invention is not limited thereto.

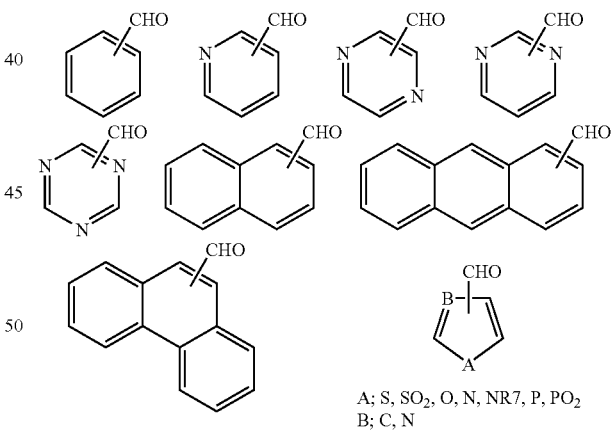

A; S, SO$_2$, O, N, NR7, P, PO$_2$
B; C, N

Then, a $R^1$ or $R^2$ substituent, for example a compound of $R^1$Br or $R^2$Br is dissolved in anhydrous THF and t-BuLi or n-BuLi is added thereto. Then, the compound C is incorporated into the mixture for reaction to prepare the compound D (2). The compound D can be reacted with acetic acid, KI, NaH$_2$PO$_2$ to prepare the compound of the formula (1).

Further, the compound C prepared as described above is reacted with activated zinc (Zn) and sodium hydroxide (NaOH) to prepare the compound E (1'). Subsequently, the compound E is reacted with NBS (N-bromosuccinimide) and dimethylformamide (DMF) to prepare the compound F (2').

Then, the compound F can be reacted with boronic acid having $R^1$ or $R^2$, $Pd(PPh_3)_4$, $K_2CO_3$ and THF to prepare the compound of the formula (1).

Furthermore, the compound of the above formula (1) can be prepared according to the following reaction scheme 2:

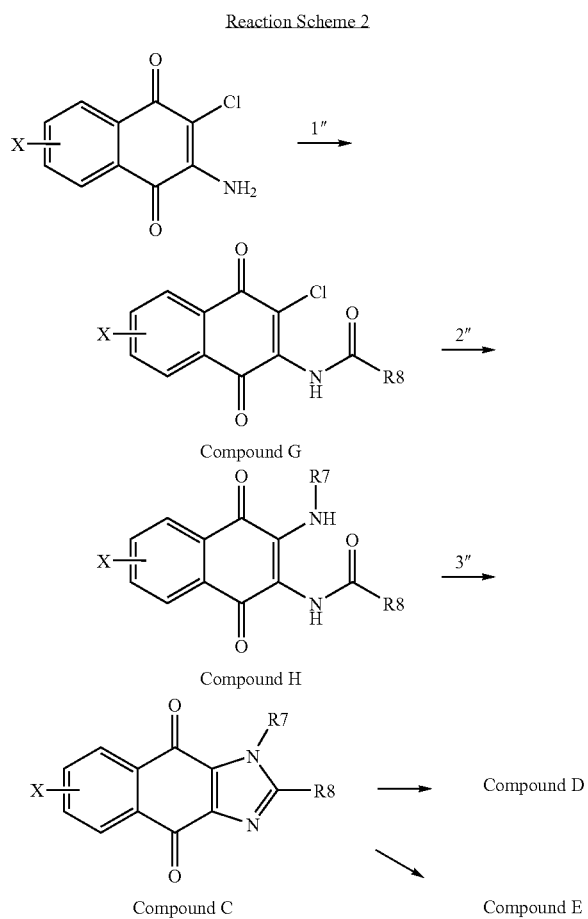

wherein X is as defined for the above reaction scheme 1; and $R^7$ and $R^8$ are as defined in the above formula (1).

Specifically, a substituted or unsubstituted 2-amino-3-chloro-1,4-naphthoquinone is reacted with acetic anhydride, alkylcarbonyl chloride ($R^8COCl$) such as a substituted acetyl chloride, or a substituted or unsubstituted benzoyl chloride to prepare the compound G (1"). A naphthoquinone compound G substituted with amide is reacted in an organic solvent such as toluene and xylene, with $R^7NH_2$ in order to introduce a $R^7NH$-group into the remaining chloro group (—Cl) to thus prepare the compound H (2"). The compound H is heated with stirring for 10 minutes to 2 hours in a solution of 2 N NaOH/EtOH to prepare the compound C (3"). This compound C can be prepared from the compound of the formula (1) in the same manner as in the above-mentioned reaction scheme 1.

Further, the invention provides an organic electronic device comprising a first electrode, a second electrode and at least one organic material layer arranged between the first electrode and the second electrode, in which at least one layer of the organic material layer comprises the compound represented by the above formula (1).

A steric structure of the compound of the above formula (1) according to the invention can be considered to be divided into two portions, A and B portions, as shown in the following figure:

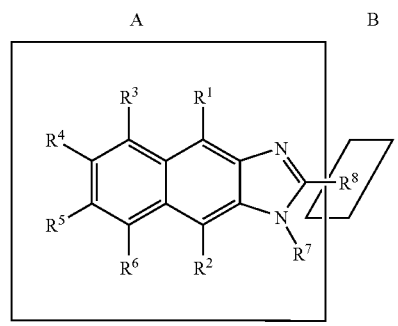

The A portion has a planar structure as in an anthracene structure as a whole in that a naphthalene group and an imidazole group form a fused ring.

An imidazole group is largely used as the substituent of an electron-injecting and/or transporting material or a light-emitting material in the organic light-emitting device and is known to have an important influence on functions of electron injection or transportation or light emission. Therefore, the A portion of the above formula (1) has n-type properties due to an imidazole group contained therein. However, the compound of the above formula (1) has a core structure in which only one of three benzene rings of anthracene is substituted with an imidazole group and various substituents are introduced at the positions of $R^1$ to $R^8$ of the core structure. Due to such structural characteristics, the compound of the formula (1) can have amphoteric properties having n-type and p-type properties, unlike a benzimidazole group simply having n-type properties. The term "n-type properties" as used herein generally refers to properties exhibiting anionic characteristics by forming electrons owing to electrically conductive characteristics depending on LUMO levels. In addition, the term "p-type properties" as used herein refers to properties exhibiting cationic characteristics by forming holes owing to electrically conductive characteristics depending on HOMO levels.

The compound of the above formula (1) having amphoteric properties can exhibit stronger n-type or p-type behavior of the whole molecule by introducing various substituents into the A or B portion. For example, when a specific substituent is introduced into the B portion of the formula (1) and the compound of the formula (1) exhibits one behavior stronger than the other behavior, the compound of the formula (1) can be a compound that more suitably meets the requirements as a hole-injecting or hole-transporting material, an electron-injecting or electron-transporting material, or a light-emitting material. For example, when $R^8$ of the B portion is substituted with an alkyl group having an amine group, a cycloalkyl group having an amine group, an aryl group having an amine group, a heteroaryl group having an amine group, and the like, the compound of the formula (1) is widely applied as a material for the hole-injecting layer and hole-transporting layer. On the other hand, when $R^8$ is substituted with a material having high electron affinity, such as an heteroaryl group, nitrile, nitro, carbonyl and amide, the compound of the formula (1) can be applied as a material for the electron-injecting or electron-transporting layer. Further, when $R^8$ is substituted with alkenyl such as anthracene, perylene, pyrene and stilbene, the compound of the formula (1) can be applied for the light-emitting layer. A principle in which various substituents are introduced at $R^8$, can be applied even when various substituents are introduced at $R^1$ to $R^7$, Further, various substituents are introduced at $R^1$ to $R^8$ of the formula (1) to decrease pi-pi interaction in the structure of the compound, thereby having effects of suppressing the formation of excited excimer or excited exciplex from materials having a flat structure.

Furthermore, various substituents can be introduced at the $R^1$ to $R^8$ positions of the above formula (1) to synthesize a compound having various energy band gaps. Therefore, the compound of the above formula (1) can form a compound that meets the requirements for the hole-injecting layer, the hole-transporting layer, the light-emitting layer, the electron-injecting layer and the electron-transporting layer by means of various substituents. In the invention, a compound having a suitable energy level according to substituents of the compound of the above formula (1), can be selected and used in an organic electronic device to thus realize a device with low drive voltage and high light efficiency.

The organic electronic device of the invention can be produced by the general production method of the organic electronic device and materials, except that the above-mentioned compound is used to form one or more organic material layer.

Hereinafter, the organic light-emitting device will be illustrated.

In one embodiment of the invention, the organic light-emitting device has a structure comprising a first electrode, a second electrode and an organic material layer arranged therebetween, and can be produced by the general production method of the organic electronic device and materials, except that the compound of the formula (1) according to the invention is used in one or more organic material layers of the organic light-emitting device. The structure of the organic light-emitting device according to the invention is illustrated in FIG. 1.

For example, the organic light-emitting device according to the invention can be produced by depositing metals or metal oxides having electrical conductivity, or metal alloys thereof on a substrate to form an anode, forming thereon an organic material layer comprising a hole-injecting layer, a hole-transporting layer, a light-emitting layer and an electron-transporting layer and then depositing a material capable of using as a cathode on the organic material layer, using a PVD (physical vapor deposition) technique such as sputtering and e-beam evaporation. In addition to this method, the organic light-emitting device can be also fabricated by sequentially depositing a cathode material, an organic material layer and an anode material, on the substrate (see International Publication No. WO 03/012890).

The organic material layer may be of a multilayer structure comprising the hole-injecting layer, the hole-transporting layer, the light-emitting layer, the electron-transporting layer and the like, but not limited thereto, and may be of a monolayer structure. Further, the organic material layer can be produced in a smaller number of layers with various polymer materials by using not a vacuum deposition method but a solvent process such as spin coating, dip coating, doctor blade coating, screen printing, inkjet printing, heat transfer method or the like.

The anode materials are preferably materials having large work function for facilitating usually hole injection into the organic material layer. Specific examples of the anode materials usable in the invention include metals such as vanadium, chrome, copper, zinc and gold or alloys thereof; metal oxides such as zinc oxide, indium oxide, indium tin oxide (ITO) and indium zinc oxide (IZO); metal/oxide composites such as $ZnO:Al$ or $SnO_2:Sb$; and conductive polymers such as poly (3-methylthiophene), poly[3,4-(ethylene-1,2-dioxy) thiophene] (PEDT), polypyrrole and polyaniline, but are not limited thereto.

The cathode materials are preferably materials having small work function for facilitating usually electron injection into the organic material layer. Specific examples of the cathode materials include metals such as magnesium, calcium, sodium, potassium, titanium, indium, yttrium, lithium, gadolinium, aluminum, silver, tin and lead or alloys thereof; and multilayered materials such as LiF/Al or $LiO_2$/Al, but are not limited thereto.

The hole-injecting material is a material facilitating hole injection from an anode at low voltage. The HOMO (highest occupied molecular orbital) level of the hole-injecting material is preferably located between the work function of the anode materials and the HOMO level of its neighboring organic material layer. Specific examples of the hole-injecting material include metal porphyrin, oligothiophene, arylamine-based organic materials, hexanitrile hexaazatriphenylene, quinacridone-based organic materials, perylene-based organic materials, anthraquinone, and polyaniline-based and polythiophene-based conductive polymers, but are not limited thereto.

The hole-transporting material is suitably a material having high hole mobility, which can transfer holes from the anode or the hole-injecting layer toward the light-emitting layer. Specific examples thereof include arylamine-based organic materials, conductive polymers and block copolymers having both conjugated portions and non-conjugated portions, but are not limited thereto.

The light-emitting material are a material capable of emitting visible light by accepting and recombining holes from the hole-transporting layer and electrons from the electron-transporting layer, preferably a material having high quantum efficiency for fluorescence or phosphorescence. Specific examples thereof include 8-hydroxyquinoline aluminum complex ($Alq_3$); carbazole-based compound; dimerized styryl compounds; BAlq; 10-hydroxybenzoquinoline-metal compounds; benzoxazole-based compound, benzthiazole-based and benzimidazole-based compound; poly(p-phenylenevinylene) (PPV)-based polymer; spiro compounds; polyfluorene, rubrene and the like, but are not limited thereto.

The electron-transporting material is suitably a material having high electron mobility, which can transfer electrons from the cathode to the light-emitting layer. Specific examples thereof include 8-hydroxyquinoline aluminum complex ($Alq_3$); organic radical compounds; and hydroxyflavone-metal complexes, but are not limited thereto.

The organic light-emitting device according to the invention may be of a top emission structure, a bottom emission structure or a top and bottom emission structure according to the materials used.

The compound according to the invention can function in an organic electronic device including an organic solar cell, an organic photoconductor and an organic transistor, according to a principle similar to that applied to the organic light-emitting device.

Advantageous Effects

The compound of the invention is a new compound in which the compound can perform functions of hole injection, hole transportation, electron injection, electron transportation, and/or light emission in an organic electronic device including an organic light-emitting device, and further can perform a function of a light-emitting host together with a suitable dopant. By applying the compound of the invention to the organic electronic device including the organic light-emitting device, it is possible to achieve excellent effects in terms of an efficiency of a device, drive voltage and stability.

MODE FOR INVENTION

Figure 1:
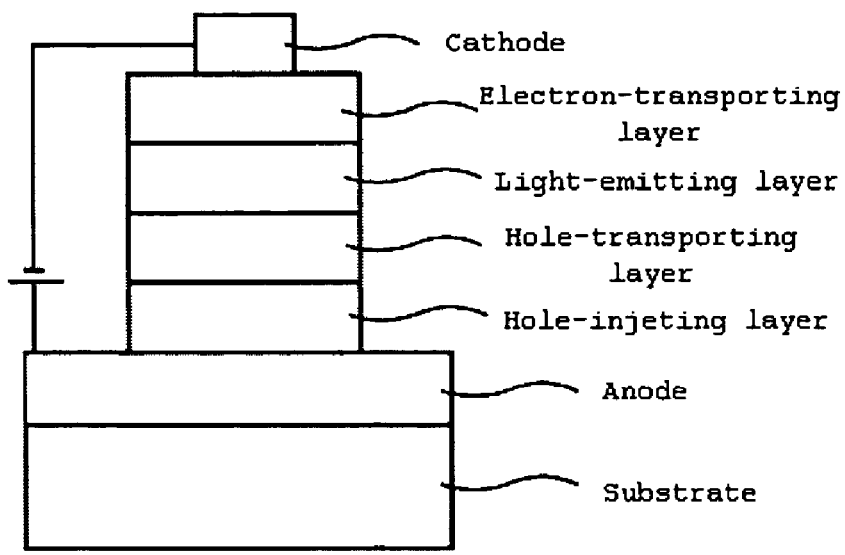
FIG. 1 illustrates a structure of an organic light-emitting device according to one embodiment of the present invention.

Hereinafter, the present invention will be described in more detail by means of Examples and Experimental Examples, but the scope of the invention is not limited thereto.

Example 1

Synthesis of Compounds of Formula (1-10)

1. Synthesis of the Compound of the Following Formula (10A)

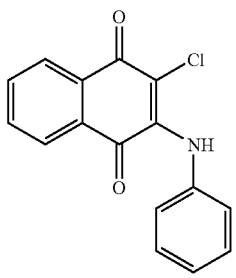

(10A)

2,3-Dichloronaphthoquinone (22.7 g, 100 mmol), aniline (9.3 g, 100 mmol), N,N-dimethylaniline (50 mL) and acetic acid (200 mL) were mixed and heated for 6 hours. The reaction mixture turned to a dark red solution as the reaction proceeded. The reactants were cooled to room temperature, and the solid formed was filtered under reduced pressure and then dried under vacuum to obtain the compound of the above formula (10A) (22 g, yield 78%).

MS: $[M+H]^+=284(Cl\times1)$

2. Synthesis of the Compound of the Following Formula (10B)

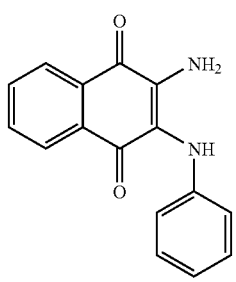

(10B)

The compound of the formula (10A) (22 g, 77.6 mmol) and sodium azide (NaN$_3$, 10.1 g, 155.2 mmol) were dissolved in dimethylformamide (DMF, 200 mL) and water (H$_2$O, 30 ml) was added thereto, and then the reactants were heated with stirring at 120° C. for 20 hours. The reactants were cooled to room temperature, and the black solid formed was filtered, washed with water and ethanol and then dried to obtain the compound of the formula (10B) as a solid (20.0 g, yield 97.6%).

3. Synthesis of the Compound of the Following Formula (10C-1)

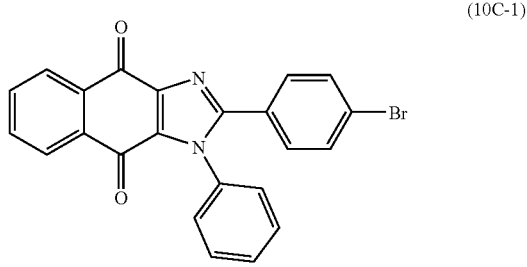

(10C-1)

The compound of the formula (10B) (5.28 g, 20 mmol), 4-bromobenzaldehyde (3.70 g, 20 mmol) and dimethylacetamide (DMAC, 80 mL) were mixed and heated for 16 hours. After removing the reaction solvent under reduced pressure, 100 mL of ethyl acetate was introduced into the reaction mixture and then the resultant was stirred to obtain the compound of the above formula (10C-1) as a solid (4.5 g, yield 53%).

MS: $[M+H]^+=429(Br\times1)$

4. Synthesis of the Compound of the Following Formula (10C-2)

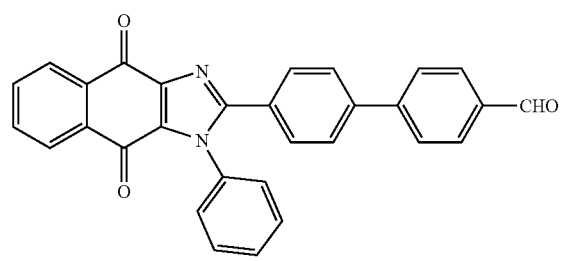

(10C-2)

The compound of the formula (10C-1) (4.50 g, 10.5 mmol), tetrahydrofuran (THF, 25 ml), 4-formylphenylboronic acid (1.80 g, 1.8 mmol), tetrakis(triphenylphosphine)palladium(0) [Pd(PPh$_3$)$_4$, 0.02 mmol, 0.02 g] and 2 M potassium carbonate (2 M K$_2$CO$_3$, 25 mL) were mixed and heated with stirring 12 hours. The reaction mixture was cooled to room temperature and a small amount of tetrahydrofuran (THF) was distilled under vacuum. Ethanol was added to the precipitate formed and the resultant was stirred, filtered, washed with ethanol and water, and then dried to obtain the compound of the above formula (10C-2) (2.5 g, yield 52%).

MS $[M+H]^+=455$

5. Synthesis of the Compound of the Following Formula (10C-3)

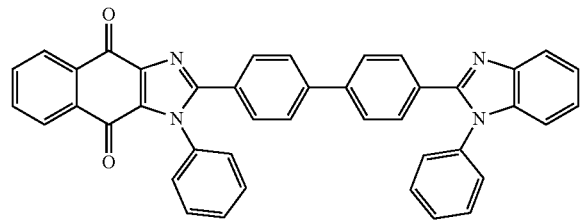

(10C-3)

The compound of the above formula (10C-2) (2.5 g, 5.5 mmol), N-phenyl-1,2-phenylenediamine (1 g, 5.5 mmol) and N,N-dimethylacetamide (30 mL) were mixed and heated at 160° C. for 10 hours. After the solvent was removed under reduced pressure, 100 mL of ethanol was added to the reaction mixture and the resultant was stirred to obtain the compound of the above formula (10C-3) as a yellow solid (2.2 g, yield 65.4%).

6. Synthesis of the Compound of the Following Formula (10D)

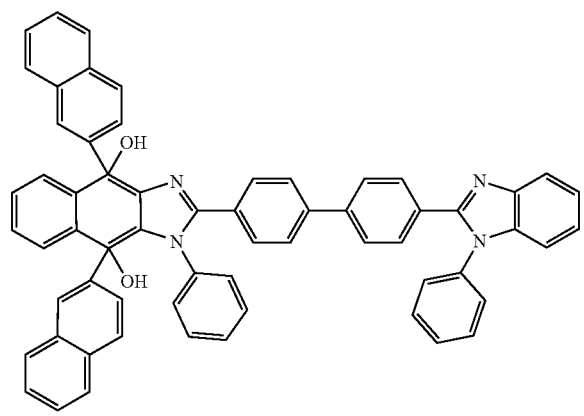

(10D)

2-Bromonaphthalene (1.8 g, 2.4 eq, 8.6 mmol) was dissolved in 40 mL of anhydrous THF. After cooling the reaction mixture to 78° C., t-BuLi (1.7 M in pentane) (3.0 eq, 10.8 mmol, 6.4 mL) was slowly added dropwise thereto and the resulting mixture was stirred for 40 minutes. Then, the compound of the formula (10C-3) (2.2 g, 3.6 mmol) prepared above in a solid state was added dropwise to a reaction vessel and then the resulting mixture was stirred for 4 hours. A water-soluble $NH_4Cl$ was introduced into the resulting mixture to carry out phase separation and extracted with THF. The extracts are dried over anhydrous $MgSO_4$ and concentrated under vacuum reduced pressure. The residue was stirred in 100 ml of ethyl ether to obtain the compound of the above formula (10D) as a solid (2.2 g, yield 70%).

7. Synthesis of the Compound of the Following Formula (1-10)

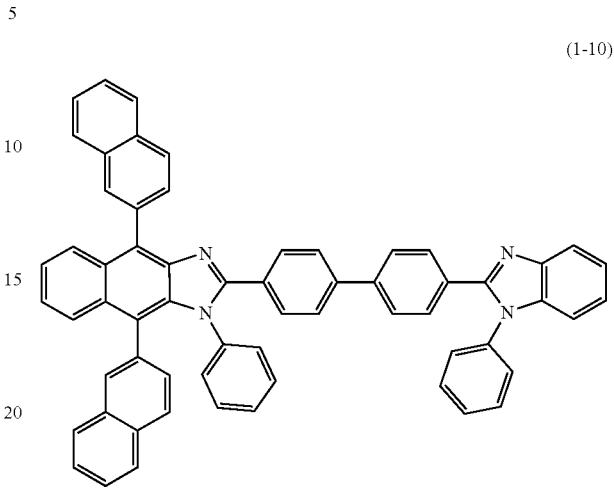

(1-10)

Figure 2:
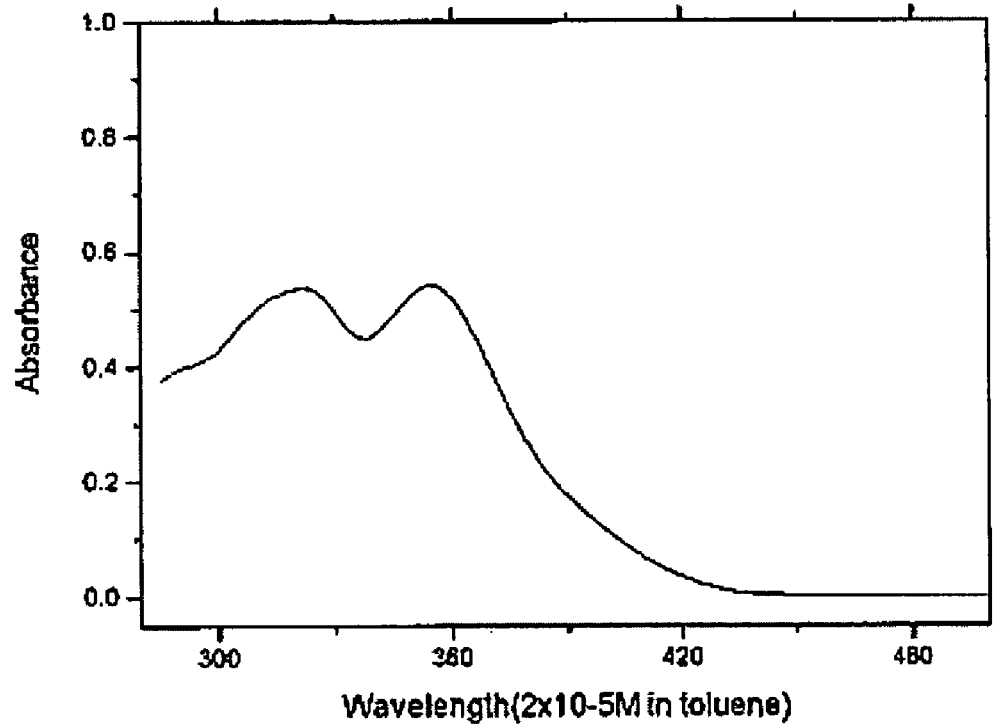
FIG. 2 shows the UV spectrum of the compound of the formula (1-10) according to the invention.

The compound of the above formula (10D) (2.2 g, 2.6 mmol) was mixed with 60 mL of acetic acid, KI (4.3 g, 26 mmol) and $NaH_2PO_2$ (5.2 g, 49 mmol), and the reaction mixture was stirred at 120° C. for 5 hours. After cooling the reaction solution, the solid formed was filtered, well washed with water and then dried to obtain the compound of the formula (1-10) (1.97 g, yield 90%). UV spectrum of the compound of the formula (1-10) was shown in FIG. 2.

Tg: 195° C. (2nd)

MS $[M+H]^+=841$

Example 2

Synthesis of Compounds of Formula (1-13)

1. Synthesis of the Compound of the Following Formula (13C)

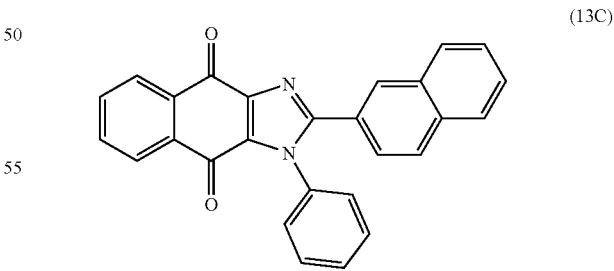

(13C)

The compound of the above formula (13C) was prepared in the same manner as in the preparation of the compound of the formula (10C-1) except that 2-formylnaphthalene was used instead of 4-bromobenzaldehyde in Example 1-3.

MS $[M+H]^+=401$

2. Synthesis of the Compound of the Following Formula (13E)

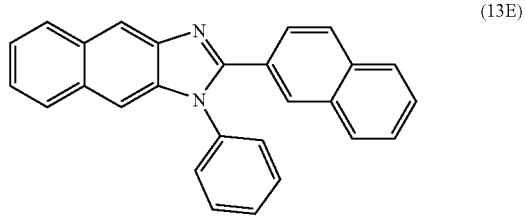

Distilled water (165 ml), sodium hydroxide (NaOH, 62 mmol, 24.8 g) and the compound of the above formula (13C) (12.2 mmol, 4.85 g) were introduced into activated zinc (Zinc, 20 g) and the reaction mixture was heated with stirring for 24 hours. Subsequently, the mixture was cooled to room temperature and filtered through Celite. The filtrate was extracted with dichloromethane (50 ml×3), dried over anhydrous magnesium sulfate and filtered under reduced pressure. The solvent was removed from the filtrate under reduced pressure, and the residue was recrystallized from ethyl ether and hexane to obtain the compound of the above formula (13E) (2.3 g, yield 52%).

MS [M+H]$^+$=371

3. Synthesis of the Compound of the Following Formula (13F)

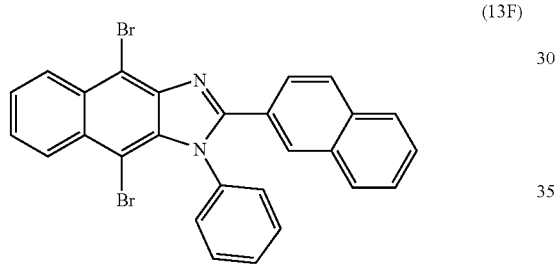

The compound of the above formula (13E) (6.2 mmol, 2.3 g) and NBS (N-bromosuccinimide) (6.4 mmol, 1.2 g) were dissolved in dimethylformamide (DMF, 70 ml) and the reaction mixture was stirred at room temperature for 40 minutes. The precipitate formed was filtered under reduced pressure to obtain the compound of the above formula (13F) (2.9 g, yield 90%).

MS [M+H]$^+$=526 (Br×2)

4. Synthesis of the Compound of the Formula (1-13)

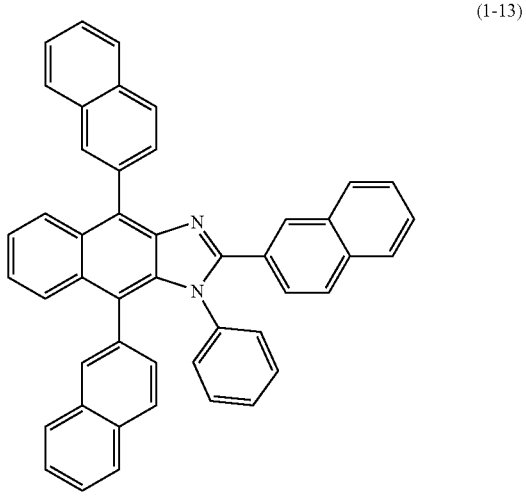

The compound of the formula (13F) prepared as described above (2.9 g, 5.5 mmol) was mixed with naphthalene-2-boronic acid (2.3 g, 13.2 mmol), Pd(PPh$_3$)$_4$ [0.038 g, 0.033 mmol] and 40 mL of 2 M K$_2$CO$_3$ and the reaction mixture was stirred in 80 mL of THF at 80° C. for 8 hours. The reaction mixture was cooled to room temperature and the excess THF was distilled off under vacuum. Then, 200 mL of ethanol was added to the reaction mixture and the resultant was stirred to obtain the compound of the formula (1-13) as a solid (2.7 g, yield 80%).

MS [M+H]$^+$=623

Example 3

Synthesis of Compound of Formula (1-38)

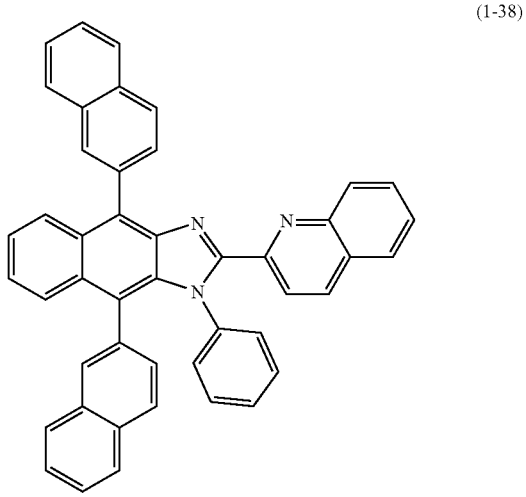

The solid compound of the formula (1-38) was prepared in the same manner as in the preparation of the compounds of the formula (10C-1), the formula (10D) and the formula (1-10) by using the compound of the above formula (10B) (5.28 g, 20 mmol) and quinoline-2-carboxaldehyde as a starting material.

Tg: 195° C., Tm: N.D (2nd)
MS: [M+H]$^+$=511

Example 4

Synthesis of Compounds of Formula (1-49)

1. Synthesis of the Compound of the Formula (49G)

To a mixture of 2-amino-3-chloro-1,4-naphthoquinone (4.4 g, 21.2 mmol) and 60 mL of acetic anhydride was added dropwise 2 mL of 98% sulfuric acid and the reaction mixture was stirred at room temperature for 3 hours. The precipitate formed was filtered, well washed with water and then dried to prepare the compound of the following formula (49G) (3.3 g, yield 63%).

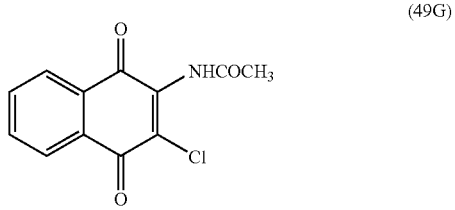

2. Synthesis of the Compound of the Formula (49H)

Aniline (1.68 g, 18 mmol) and 70 mL of toluene were introduced into the compound of the above formula (49G) (3.3 g, 13.3 mmol) and the reaction mixture was stirred at room temperature for 16 hours. To the reaction solution was added 100 mL of n-hexane, and the resulting mixture was stirred for 10 minutes, filtered and dried to prepare an intermediate of the following formula (49H) (3.2 g, yield 92%).

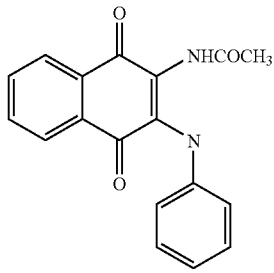

(49H)

The results for mass analysis of the intermediate were as follows:
MS [M−H]⁻=305, MS [M+H]⁺=307

3. Synthesis of the Compound of the Formula (49C)

30 mL of 2 N NaOH and 100 mL of ethanol were introduced into the compound of the above formula (49H) (3.2 g, 12.2 mmol) and the reaction mixture was heated with stirring for 30 minutes. The light green solid formed was filtered, sequentially washed with water and ethanol and then dried to prepare the compound of the following formula (49C) (2.3 g, yield 66%).

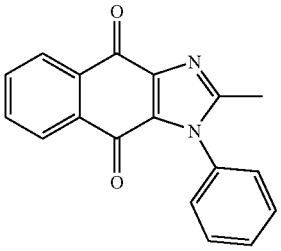

(49C)

MS [M+H]⁺=289

4. Synthesis of the Compound of the Formula (1-49)

Then, the compound of the formula (1-49) (1.7 g) was prepared in the same manner as in the preparation of the compounds of the formula (10D) and the formula (1-10) by using the compound of the above formula (49C). The results for mass analysis of the compound were as follows:

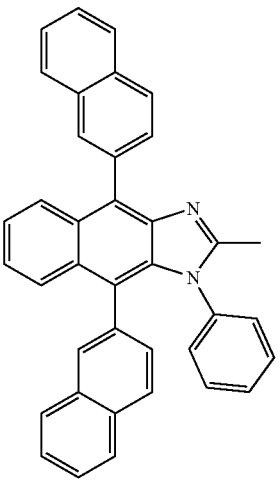

(1-49)

MS [M+H]⁺=511

Experimental Example 1

A glass substrate on which a thin film of ITO (indium tin oxide) was coated to a thickness of 1500 Å was immersed in distilled water containing a detergent to wash the substrate with ultrasonic waves for 30 minutes (At this time, the detergent was a product commercially available from Fisher Co. and the distilled water has been filtered twice by using a filter commercially available from Millipore Co.). Next, washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried and transferred to a plasma cleaner. Then, the substrate was cleaned for 5 minutes by using oxygen plasma and transferred to a vacuum deposition device.

On the ITO transparent electrode thus prepared, hexanitrile hexaazatriphenylene was coated to a thickness of 500 Å by thermal vacuum deposition, thereby forming a hole-injecting layer. Next, NPB as a hole-transporting material was coated thereon to a thickness of 400 Å by vacuum deposition. Additionally, an Alq₃ compound was coated thereon to a thickness of 300 Å by vacuum deposition to form a light-emitting layer.

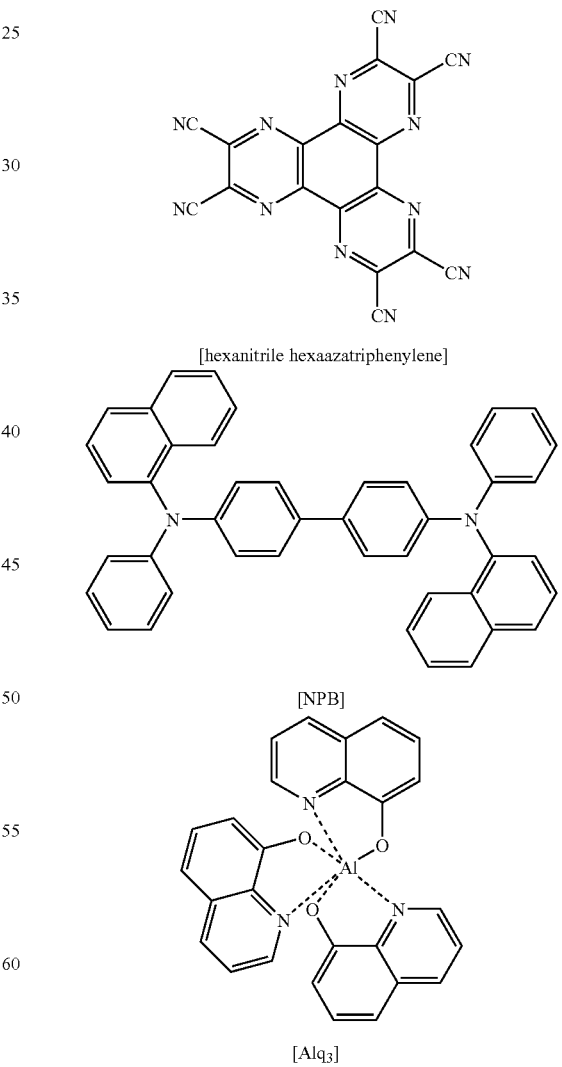

[hexanitrile hexaazatriphenylene]

[NPB]

[Alq₃]

On the light-emitting layer, the compound of the formula (1-10) prepared in Example 1 was coated to a thickness of 200

Å by vacuum deposition to form an electron-injecting/transporting layer. Next, on the electron-injecting/transporting layer, lithium fluoride (LiF) and aluminum were sequentially vacuum-deposited to a thickness of 12 Å and 2000 Å, respectively, to form a cathode.

In the above process, deposition rate of each organic material was maintained at 1 Å/sec and deposition rates of lithium fluoride and aluminum were maintained at 0.2 Å/sec and 3 to 7 Å/sec, respectively.

When a forward electric field of 6.7 V was applied to the organic light-emitting device prepared above, green light emission was observed with x=0.34 and y=0.51 based on the 1931 CIE color coordinate at a current density of 50 mA/cm$^2$. When a forward electric field of 7.7 V was applied, green light emission of 3.9 cd/A was observed at a current density of 100 mA/cm$^2$.

Experimental Example 2

On the ITO electrode prepared as described in Experimental Example 1, hexanitrile hexaazatriphenylene, 4,4'-bis [N-(1-naphthyl)-N-phenylamino]biphenyl (NPB), the compound of the formula (1-13) prepared in Example 2 and Alq$_3$ were sequentially coated to thicknesses of 500 Å, 400 Å, 200 Å and 300 Å by thermal vacuum deposition, thereby forming a hole-injecting layer, a hole-transporting layer, a light-emitting layer and an electron-transporting layer in this order. Next, on the electron-transporting layer, lithium fluoride (LiF) and aluminum were sequentially vacuum-deposited to a thickness of 12 Å and 2000 Å, respectively, to form a cathode. Thus, the organic light-emitting device was prepared.

When a forward electric field of 6.2 V was applied to the organic light-emitting device prepared above, blue light emission was observed with x=0.16 and y=0.2 based on the 1931 CIE color coordinate at a current density of 50 mA/cm$^2$. When a forward electric field of 6.7 V was applied, blue light emission of 2.3 cd/A was observed at a current density of 100 mA/cm$^2$.

The invention claimed is:

1. An imidazole derivative represented by the following formula (1):

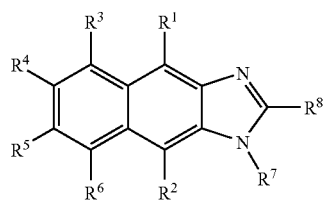

(1)

wherein $R^1$ and $R^2$ are each independently or simultaneously selected from the group consisting of an alkenyl group substituted with an aryl group, a phenyl group, a biphenyl group, a naphthyl group, a phenyl group substituted with —CN, a phenyl group substituted with a heterocyclic group, and a substituted or unsubstituted heterocyclic group;

$R^3$ to $R^6$ are each independently or simultaneously selected from the group consisting of a hydrogen atom, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a substituted or unsubstituted aliphatic cyclic group, a substituted or unsubstituted silicon group, a substituted or unsubstituted boron group, an amino group, a nitrile group, a nitro group, a halogen group, an amide group and an ester group;

$R^7$ is selected from the group consisting of a substituted or unsubstituted alkyl group, a substituted or unsubstituted aryl group, a substituted or unsubstituted heterocyclic group, a substituted or unsubstituted aliphatic cyclic group, and a substituted or unsubstituted silicon group; and $R^8$ is selected from the group consisting of an alkyl group; an aryl group which is unsubstituted or substituted with an alkyl group, an alkenyl group, —CN, an aryl group, —BRR' or —SiRR'R"; and a heterocyclic group selected from the group consisting of the following formulae:

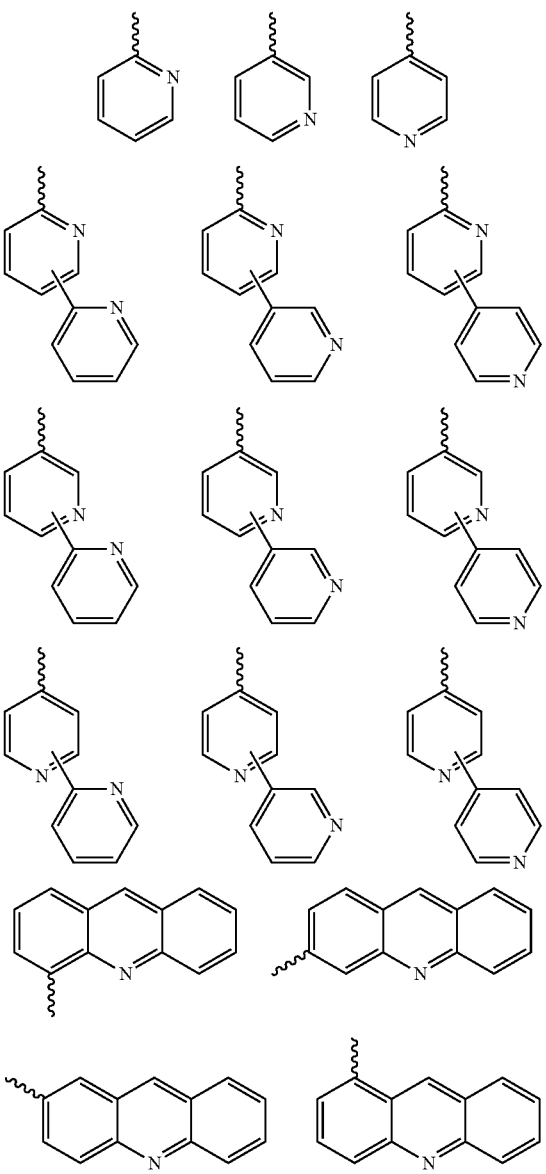

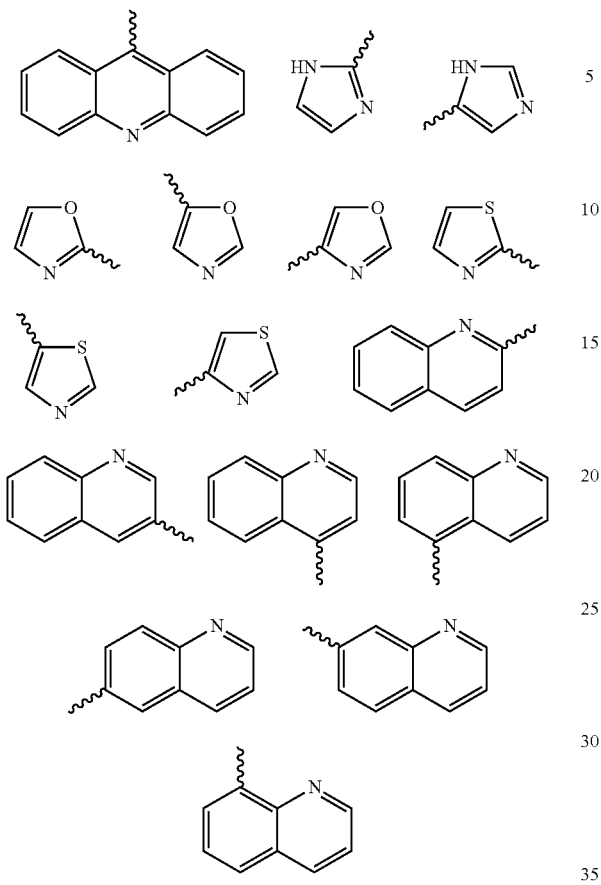

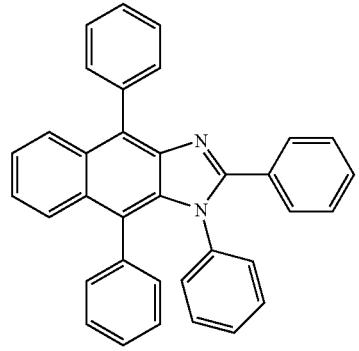
(1-1)

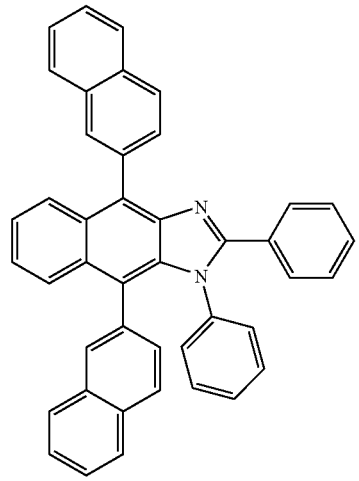
(1-2)

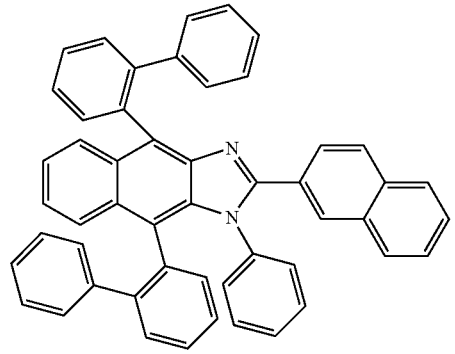
(1-3)

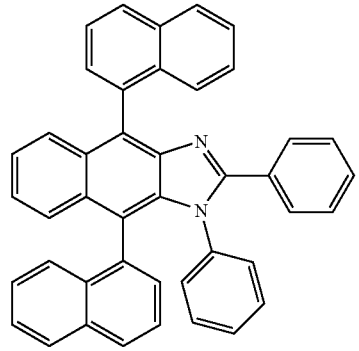
(1-4)

the heterocyclic group being unsubstituted or substituted with —CN, an aryl group, a heterocyclic group (wherein the heterocyclic group directly bonds to the formulae for $R^8$ via a carbon atom), an aliphatic cyclic group, —BRR' or —SiRR'R" (wherein R, R' and R" are the same or different from each other and are independently selected from a $C_1$ to $C_{20}$ alkyl group, a $C_6$ to $C_{20}$ aryl group, and a $C_6$ to $C_{20}$ aryl group substituted with a $C_1$ to $C_{20}$ alkyl group).

2. The imidazole derivative according to claim 1, wherein $R^3$ to $R^6$ are each selected from the group consisting of a hydrogen atom, a nitrile group, a substituted or unsubstituted aryl group, a substituted or unsubstituted arylamine group, and a substituted or unsubstituted heterocyclic group; and
$R^7$ is selected from the group consisting of an alkyl group and an aryl group.

3. The imidazole derivative according to claim 1, wherein $R^3$ to $R^6$ are a hydrogen atom; and
$R^7$ is selected from the group consisting of an alkyl group and an aryl group.

4. The imidazole derivative according to claim 1, wherein the compound of the formula (1) is selected from the group consisting of the compounds of the following formulae:

(1-5)
(1-6)
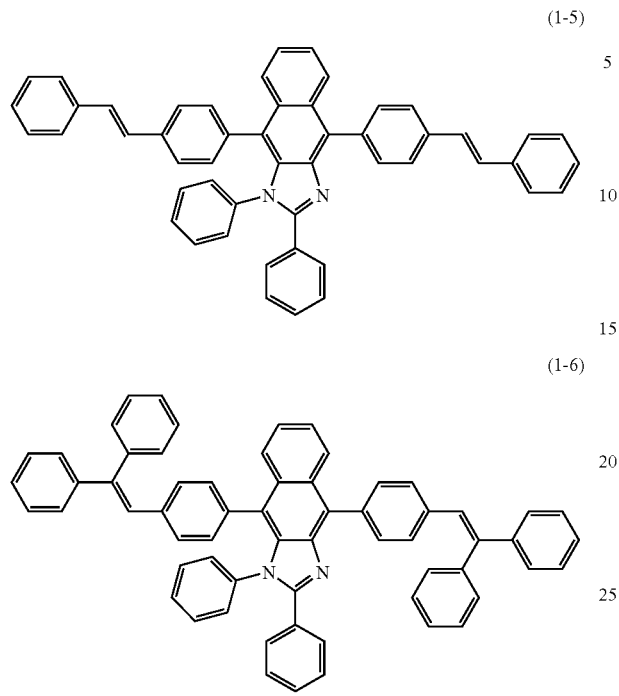
(1-9)
(1-10)
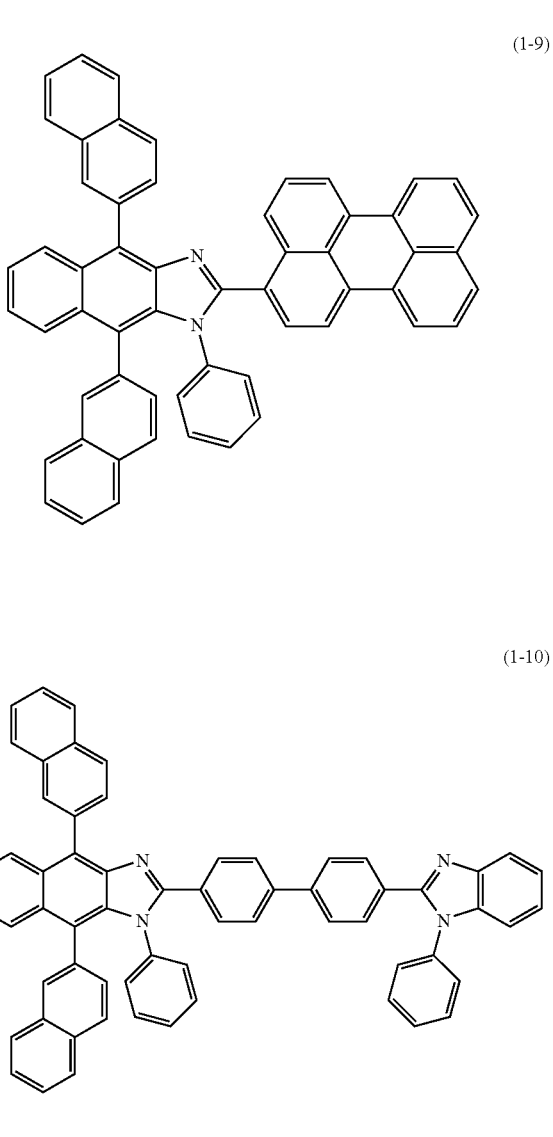
(1-7)
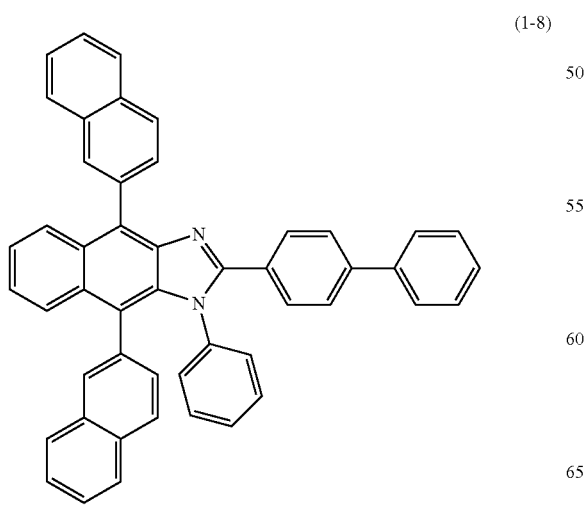
(1-8)
(1-11)
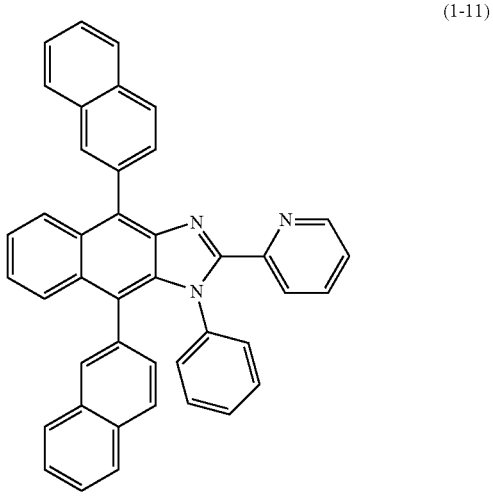

-continued
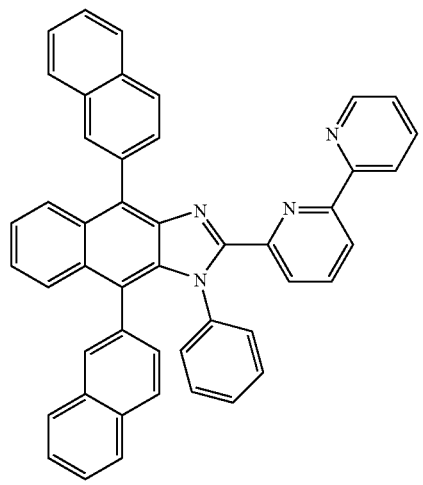
(1-12)
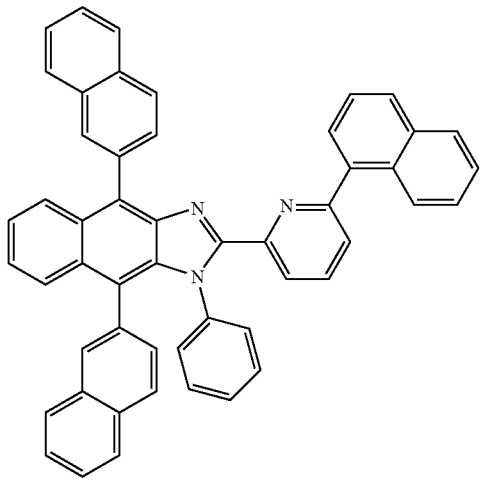
(1-15)
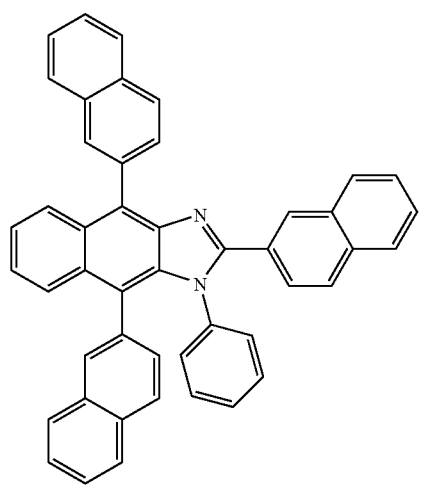
(1-13)
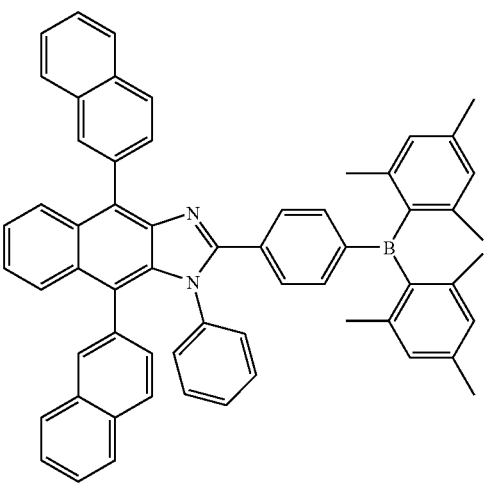
(1-16)
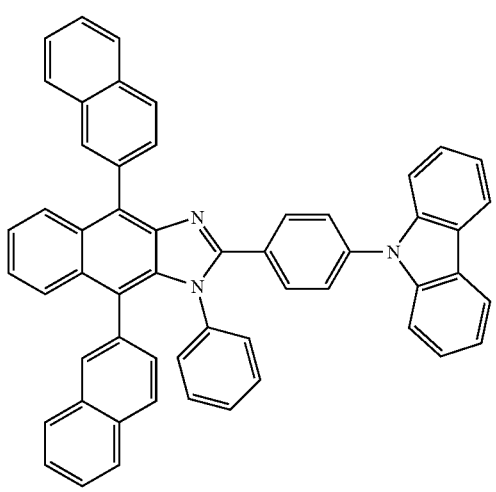
(1-14)
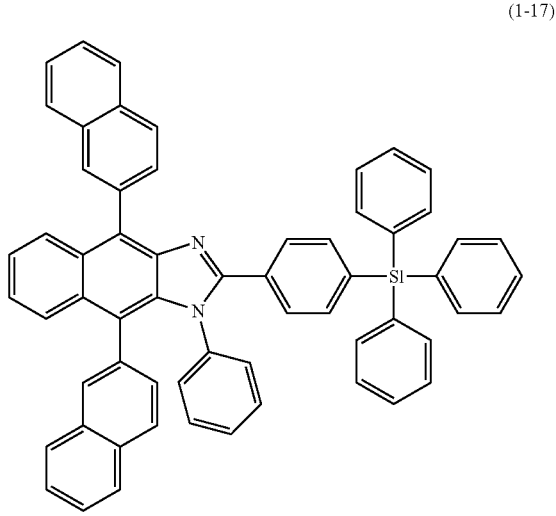
(1-17)

(1-18)
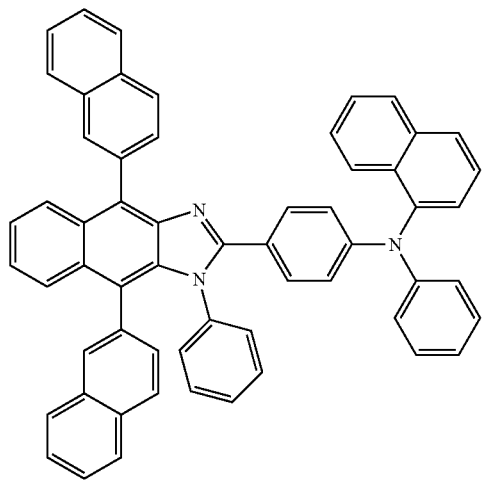
(1-19)
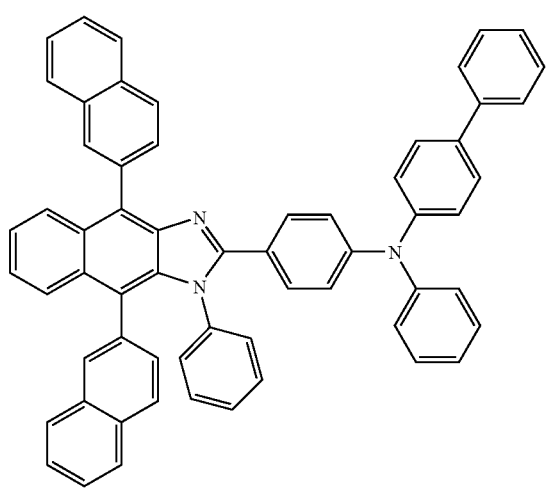
(1-20)
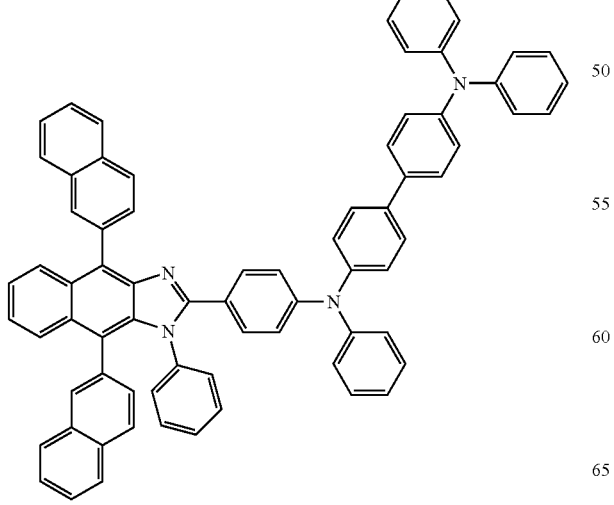
(1-21)
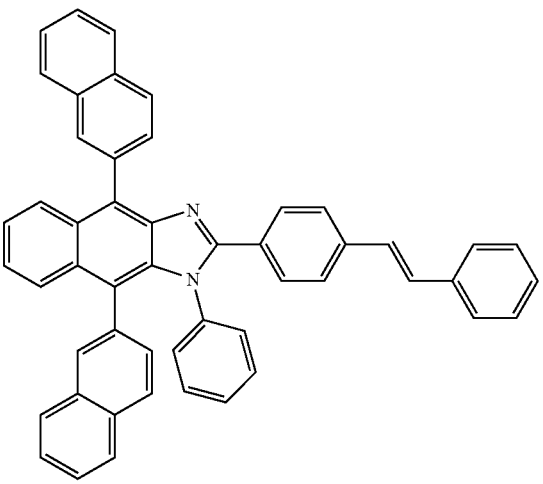
(1-22)
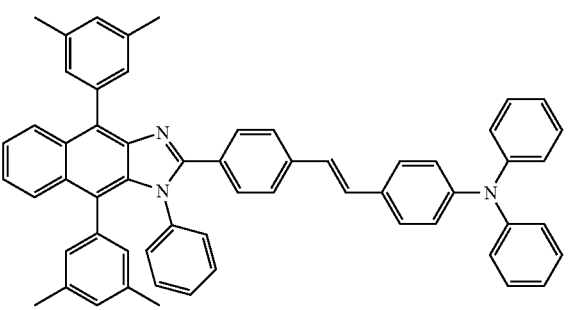
(1-23)
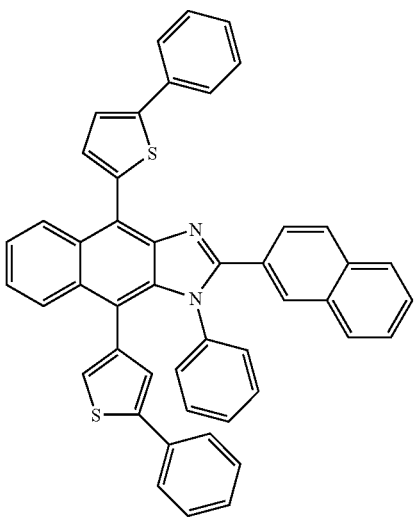

(1-24)
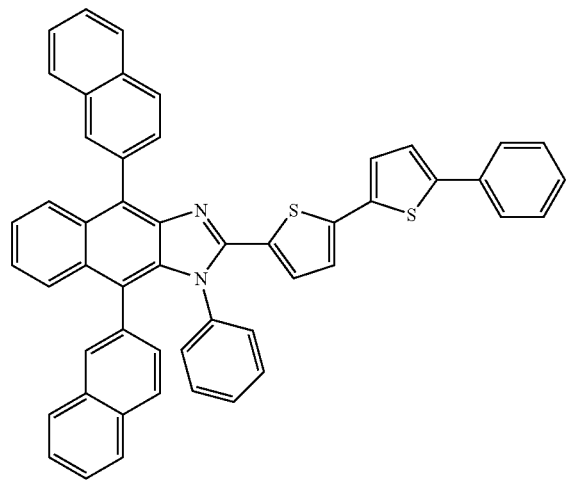
(1-25)
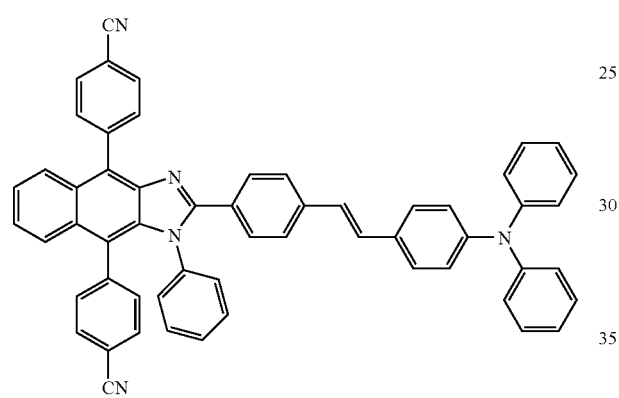
(1-26)
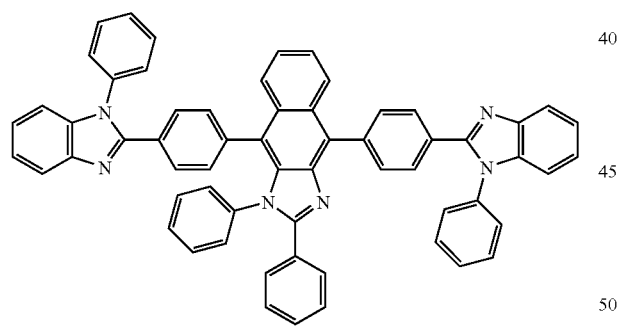
(1-27)
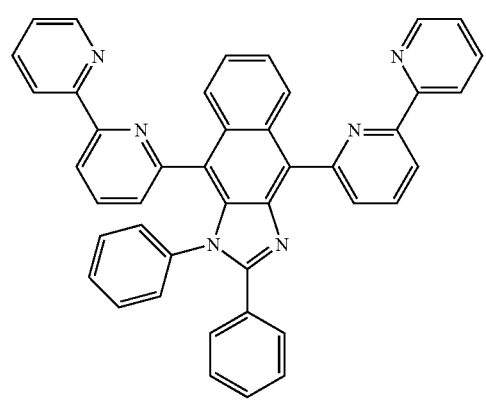
(1-28)
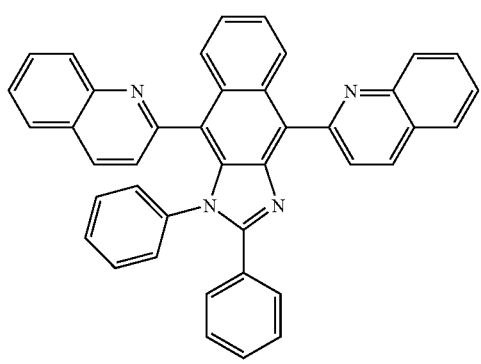
(1-29)
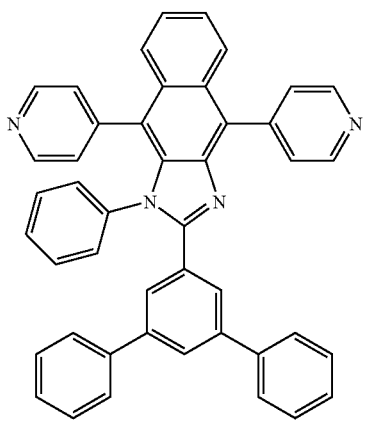
(1-30)
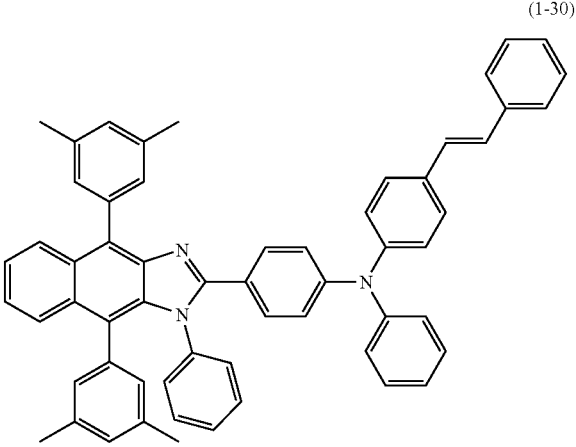
(1-31)
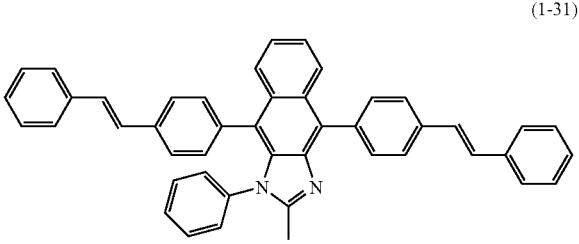

-continued
(1-32)
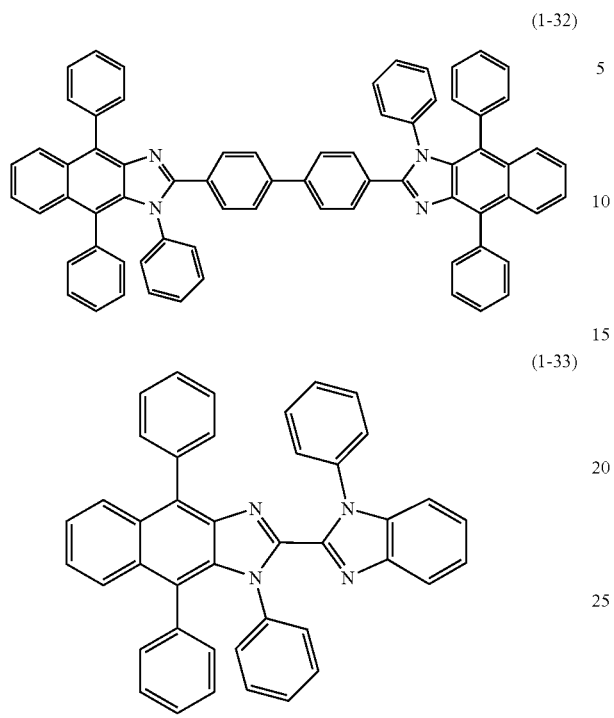
(1-33)
(1-34)
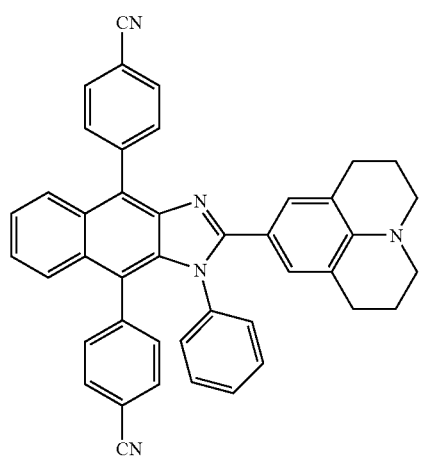
(1-35)
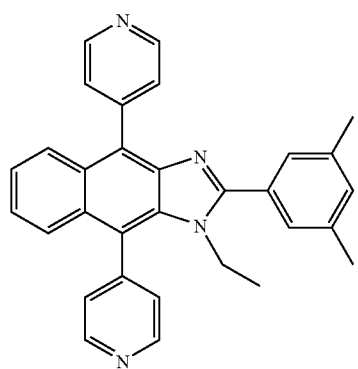
-continued
(1-36)
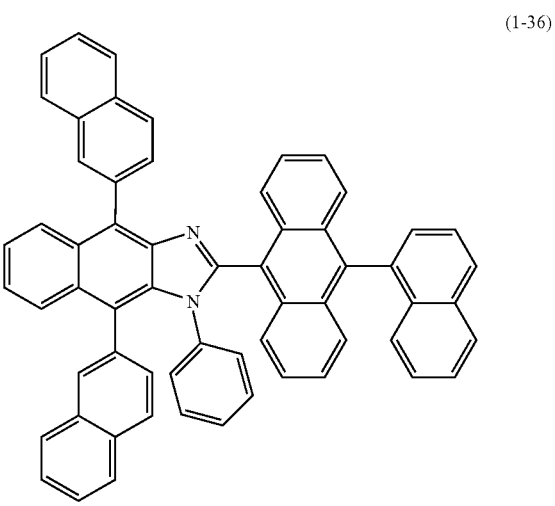
(1-37)
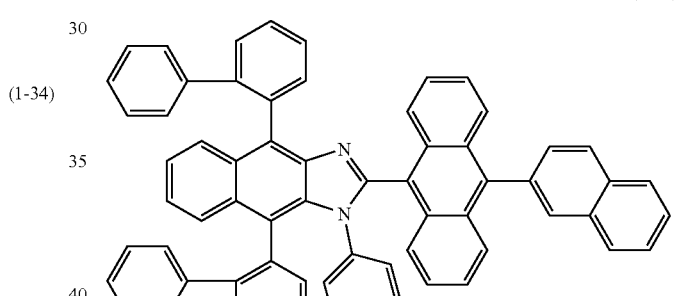
(1-38)
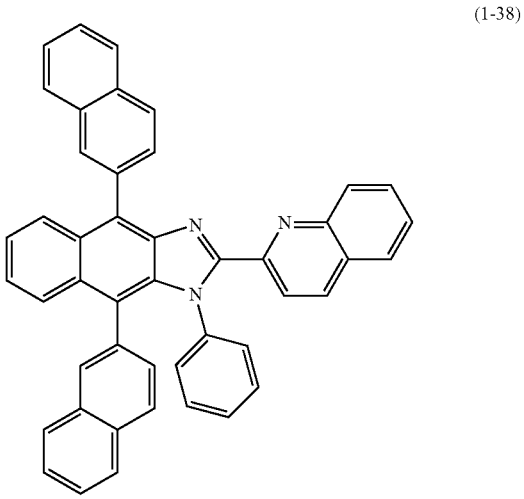

(1-39)
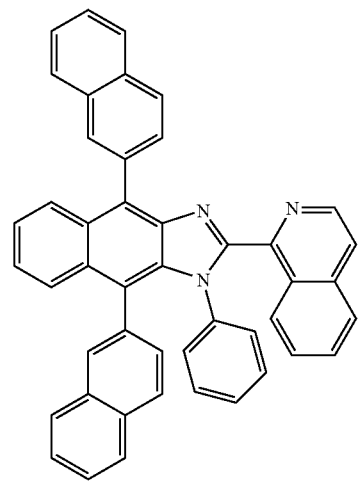
(1-40)
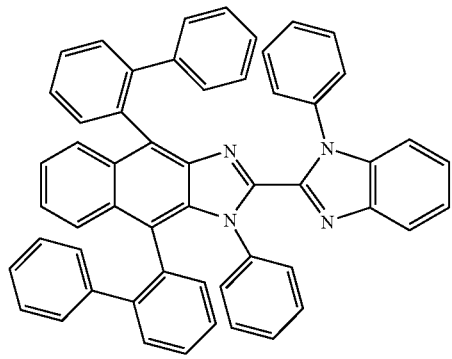
(1-41)
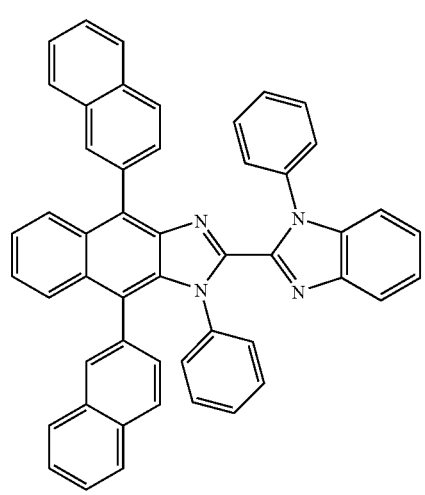
(1-42)
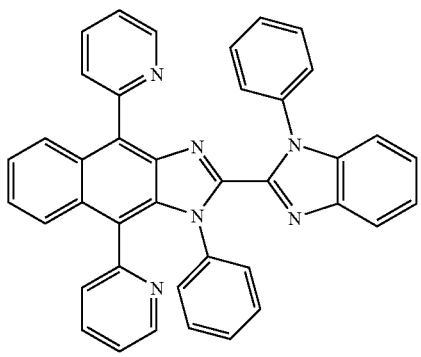
(1-43)
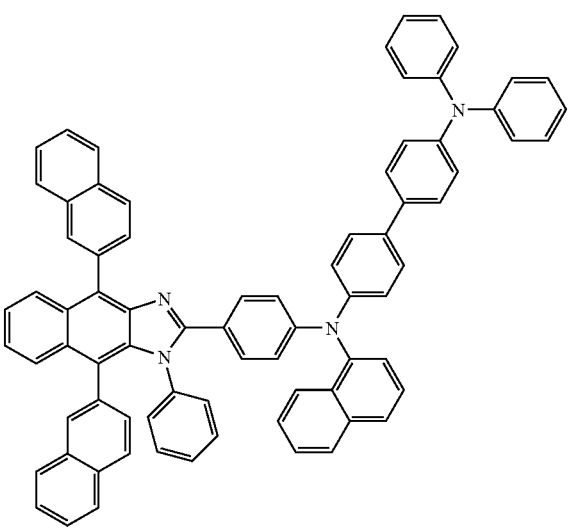
(1-44)
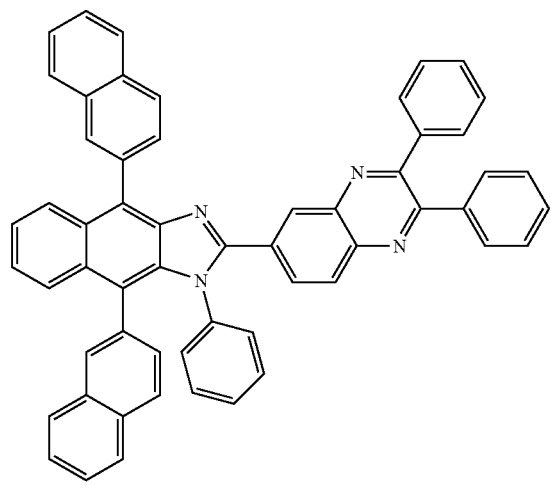

(1-45)
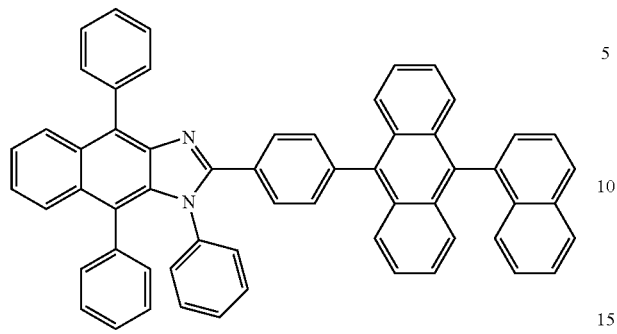
(1-46)
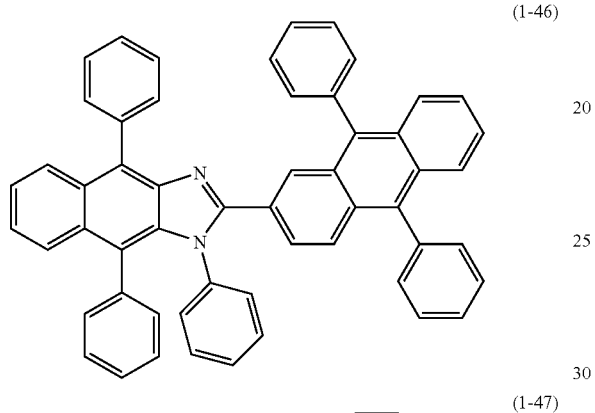
(1-47)
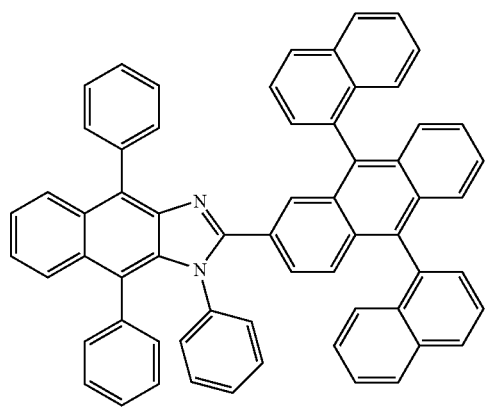
(1-48)
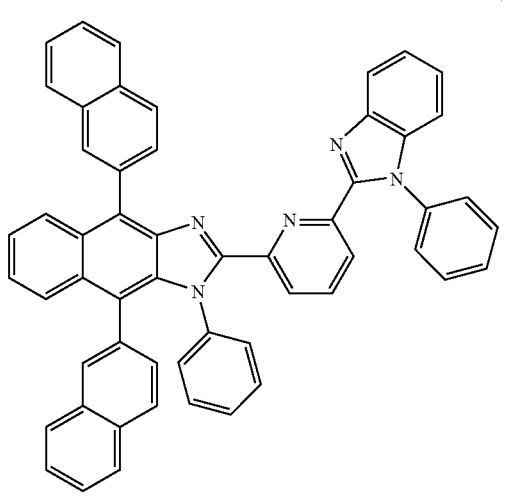
(1-49)
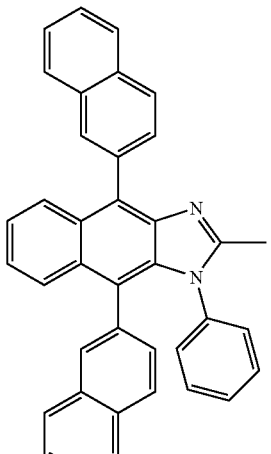
(1-50)
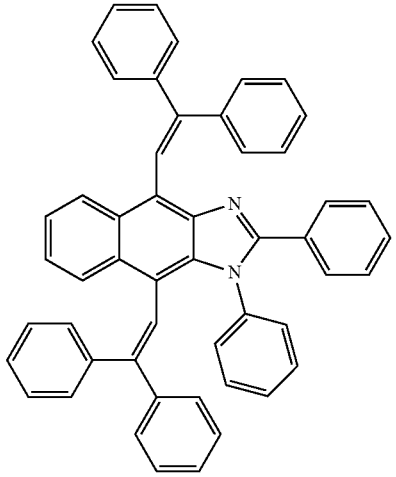
(1-51)
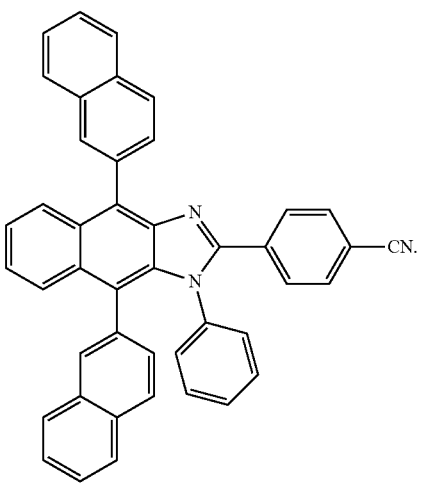
5. An organic electronic device comprising a first electrode, a second electrode and at least one organic material layer arranged between the first electrode and the second electrode, in which the at least one layer of the organic material layer comprises a compound represented by the following formula (1):

(1)

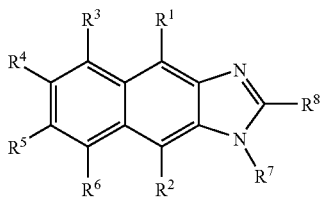

wherein $R^1$ and $R^2$ are each independently or simultaneously selected from the group consisting of an alkenyl group substituted with an aryl group, a phenyl group, a biphenyl group, a naphthyl group, a phenyl group substituted with —CN, a phenyl group substituted with a heterocyclic group, and a substituted or unsubstituted heterocyclic group;

$R^3$ to $R^6$ are each independently or simultaneously selected from the group consisting of a hydrogen atom, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a substituted or unsubstituted aliphatic cyclic group, a substituted or unsubstituted silicon group, a substituted or unsubstituted boron group, an amino group, a nitrile group, a nitro group, a halogen group, an amide group and an ester group;

$R^7$ is selected from the group consisting of a substituted or unsubstituted alkyl group, a substituted or unsubstituted aryl group, a substituted or unsubstituted heterocyclic group, a substituted or unsubstituted aliphatic cyclic group, and a substituted or unsubstituted silicon group; and $R^8$ is selected from the group consisting of an alkyl group; an aryl group which is unsubstituted or substituted with an alkyl group, an alkenyl group, —CN, an aryl group, —BRR' or —SiRR'R"; and a heterocyclic group selected from the group consisting of the following formulae:

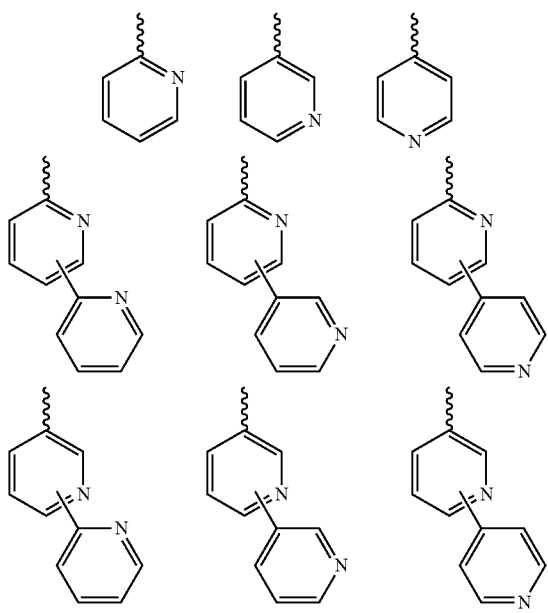

the heterocyclic group being unsubstituted or substituted with —CN, an aryl group, a heterocyclic group (wherein the heterocyclic group directly bonds to the formulae for $R^8$ via a carbon atom), an aliphatic cyclic group, —BRR' or —SiRR'R" (wherein R, R' and R" are the same or different from each other and are independently selected from a $C_1$ to $C_{20}$ alkyl group, a $C_6$ to $C_{20}$ aryl group, and a $C_6$ to $C_{20}$ aryl group substituted with a $C_1$ to $C_{20}$ alkyl group).

6. The organic electronic device according to claim 5, wherein the organic material layer comprises an electron injecting and transporting layer, and the electron injecting and transporting layer comprises the compound of the formula (1).

7. The organic electronic device according to claim 5, wherein the organic material layer comprises a light-emitting layer and the light-emitting layer comprises the compound of the formula (1).

8. The organic electronic device according to claim 5, wherein the organic material layer comprises a hole-transporting layer and the hole-transporting layer comprises the compound of the formula (1).

9. The organic electronic device according to claim 5, wherein the organic material layer comprises a layer simultaneously performing electron injection/transportation and light emission, and the layer comprises the compound of the formula (1).

10. The organic electronic device according to claim 5, wherein the organic electronic device is selected from the group consisting of an organic light-emitting device, an organic solar cell, an organic photoconductor (OPC) and an organic transistor.

11. A method for preparing the compound of the formula (1) according to claim 1, comprising the steps of:
 a) introducing each of an amino group having $R^7$ and an amino group ($NH_2$), respectively, at the 2- and the 3-carbon position of a substituted or unsubstituted naphthoquinone and introducing $R^8$ at the amino group ($NH_2$);
 b) forming an imidazole group by linking chains of the portions at which $R^7$ and $R^8$ are introduced, of the compound obtained in the above a);
 c) converting the compound obtained in the above b) to a dialcohol derivative; and
 d) reducing the compound obtained in the above c) to form a naphthalene group.

12. A method for preparing the compound of the formula (1) according to claim 1, comprising the steps of:
 a) introducing each of an amino group having $R^7$ and an amino group ($NH_2$), respectively, at the 2- and the 3-carbon position of a substituted or unsubstituted naphthoquinone and introducing $R^8$ at the amino group ($NH_2$);
 b) forming an imidazole group by linking chains of the portions at which $R^7$ and $R^8$ are introduced, of the compound obtained in the above a);
 c) reducing the compound obtained in the above b) to form a naphthalene group;
 d) introducing a bromo group at the 8- or the 9-carbon position of the compound obtained in the above c); and
 e) introducing a substituent at the position of the compound obtained in the above d), in which a bromo group is introduced, with boronic acid.

* * * * *